(12) United States Patent
Kolberg et al.

(10) Patent No.: US 12,082,778 B2
(45) Date of Patent: Sep. 10, 2024

(54) ENDOSCOPE HEAD

(71) Applicant: Digital Endoscopy GmbH, Friedberg (DE)

(72) Inventors: Stefan Kolberg, Friedberg-Bachern (DE); Anh Minh Do, Munich (DE); Thomas Viebach, Waidhofen (DE); Tilman Schröter, Olching (DE); Alex Fett, Augsburg (DE); Harald Huber, Augsburg (DE); Wolfgang Mayer, Nördlingen (DE); Marc Henzler, Mühlheim/Donau (DE)

(73) Assignee: Digital Endoscopy GmbH, Friedberg (DE)

( * ) Notice: Subject to any disclaimer, the term of this patent is extended or adjusted under 35 U.S.C. 154(b) by 9 days.

(21) Appl. No.: 17/452,755

(22) Filed: Oct. 28, 2021

(65) Prior Publication Data

US 2022/0047149 A1 Feb. 17, 2022

Related U.S. Application Data

(63) Continuation of application No. 15/114,056, filed as application No. PCT/EP2015/079079 on Dec. 9, 2015, now Pat. No. 11,278,187.

(30) Foreign Application Priority Data

Aug. 7, 2015 (DE) .......................... 102015113016.5

(51) Int. Cl.
*A61B 1/00* (2006.01)
*A61B 1/018* (2006.01)

(52) U.S. Cl.
CPC ........ *A61B 1/00098* (2013.01); *A61B 1/0011* (2013.01); *A61B 1/00137* (2013.01); *A61B 1/00177* (2013.01); *A61B 1/018* (2013.01)

(58) Field of Classification Search
CPC . A61B 1/00098; A61B 1/018; A61B 1/00137; A61B 1/00101; A61M 25/0067; A61M 25/0133; A61M 25/0147
See application file for complete search history.

(56) References Cited

U.S. PATENT DOCUMENTS 3,549,806 A 12/1970 Wood
3,605,725 A 9/1971 Bentov
(Continued)

FOREIGN PATENT DOCUMENTS

CN 1286664 A 3/2001
CN 2762381 Y 3/2006
(Continued)

OTHER PUBLICATIONS

International Search Report issued on Oct. 8, 2014 for International Application No. PCT/EP2014/065587.
(Continued)

*Primary Examiner* — Alexandra L Newton
(74) *Attorney, Agent, or Firm* — Knobbe, Martens, Olson & Bear, LLP

(57) ABSTRACT

The invention relates to an endoscope head comprising an endoscope head body in which at least one working channel is formed, wherein a pivot member actuatable from the proximal side is provided on the distal side of the endoscope head body, wherein an Albarran lever capable of being pivoted is provided at the distal end portion of the working channel.

20 Claims, 15 Drawing Sheets

(56) References Cited

U.S. PATENT DOCUMENTS

| | | | |
|---|---|---|---|
| 4,241,729 A | 12/1980 | Aoshiro | |
| 4,404,963 A | 9/1983 | Kohri | |
| 4,415,767 A | 11/1983 | Gill et al. | |
| 4,670,009 A | 6/1987 | Bullock | |
| 5,245,133 A | 9/1993 | DeCarlo et al. | |
| 5,562,600 A | 10/1996 | Matsuno | |
| 5,569,157 A * | 10/1996 | Nakazawa | A61B 1/00098 600/106 |
| 5,588,950 A | 12/1996 | Sano | |
| 5,630,419 A | 5/1997 | Ranalletta | |
| 5,674,181 A | 10/1997 | Iida | |
| 6,383,132 B1 | 5/2002 | Wimmer | |
| 6,547,722 B1 | 4/2003 | Higuma et al. | |
| 6,582,361 B2 | 6/2003 | Hirano | |
| 6,716,160 B2 | 4/2004 | Mitsumori | |
| 7,179,223 B2 | 2/2007 | Motoki et al. | |
| 7,198,599 B2 | 4/2007 | Goto et al. | |
| 7,841,880 B2 | 11/2010 | Ikeda | |
| 11,278,187 B2 | 3/2022 | Kolberg et al. | |
| 2001/0025135 A1 | 9/2001 | Naito et al. | |
| 2002/0040180 A1 | 4/2002 | Hirano | |
| 2002/0115907 A1 | 8/2002 | Mitsumori | |
| 2003/0092965 A1 | 5/2003 | Konomura et al. | |
| 2004/0015050 A1 | 1/2004 | Goto et al. | |
| 2005/0004434 A1 | 1/2005 | Bob et al. | |
| 2006/0116550 A1 | 6/2006 | Noguchi et al. | |
| 2006/0135851 A1 | 6/2006 | Yamazaki | |
| 2006/0199999 A1 | 9/2006 | Ikeda | |
| 2006/0252993 A1 | 11/2006 | Freed | |
| 2007/0099500 A1 | 5/2007 | Pilvisto et al. | |
| 2007/0156018 A1 | 7/2007 | Krauter et al. | |
| 2007/0221701 A1 | 9/2007 | Ortiz | |
| 2007/0282371 A1 | 12/2007 | Lee et al. | |
| 2009/0209820 A1 | 8/2009 | Tanaka | |
| 2009/0286412 A1 | 11/2009 | Ikeda | |
| 2010/0168560 A1 | 7/2010 | Hauck et al. | |
| 2011/0288372 A1 | 11/2011 | Petersen | |
| 2011/0313252 A1 | 12/2011 | Lin | |
| 2012/0170767 A1 | 7/2012 | Astrom et al. | |
| 2012/0209068 A1 | 8/2012 | Hosaka et al. | |
| 2014/0148646 A1 | 5/2014 | Inada | |
| 2014/0276666 A1 | 9/2014 | Malkowski | |
| 2015/0057537 A1 | 2/2015 | Dillon et al. | |
| 2015/0173711 A1 | 6/2015 | Hiraoka | |
| 2015/0238068 A1 | 6/2015 | Rose et al. | |
| 2016/0270633 A1* | 9/2016 | Iwasaka | A61B 1/00098 |
| 2016/0270636 A1* | 9/2016 | Iwasaka | A61B 1/00137 |
| 2016/0270637 A1 | 9/2016 | Tanaka et al. | |
| 2017/0127915 A1 | 5/2017 | Viebach et al. | |
| 2019/0059702 A1 | 2/2019 | Hosogoe | |
| 2019/0117045 A1* | 4/2019 | Hosogoe | A61B 1/00 |
| 2019/0223697 A1 | 7/2019 | Hosogoe et al. | |
| 2019/0223698 A1 | 7/2019 | Hosogoe et al. | |

FOREIGN PATENT DOCUMENTS

| | | |
|---|---|---|
| CN | 102307510 A | 1/2012 |
| CN | 102697445 A | 1/2012 |
| CN | 102401995 A | 4/2012 |
| CN | 202748535 U | 2/2013 |
| CN | 103153152 A | 6/2013 |
| CN | 103211566 A | 6/2013 |
| CN | 104042282 A | 9/2014 |
| CN | 104780824 A | 7/2015 |
| DE | 6905185 U | 4/1972 |
| DE | 3446698 A1 | 7/1985 |
| DE | 19627016 C1 | 2/1998 |
| DE | 69725670 T2 | 7/2004 |
| DE | 10148099 B4 | 6/2006 |
| DE | 102009060500 A1 | 7/2011 |
| DE | 102010034623 A1 | 2/2012 |
| DE | 102012009332 A1 | 11/2013 |
| DE | 102013224683 A1 | 6/2015 |
| DE | 10 2019 108078 | 4/2019 |
| DE | 10 2019 105671 | 6/2019 |
| EP | 0028396 B1 | 4/1981 |
| EP | 0055394 A1 | 7/1982 |
| EP | 1475031 A1 | 11/2004 |
| EP | 1759626 A2 | 3/2007 |
| ES | 2356497 T3 | 4/2011 |
| JP | S 4827116 A | 8/1973 |
| JP | S 61118713 A | 6/1986 |
| JP | S 62227312 A | 10/1987 |
| JP | H 05253177 A | 9/1994 |
| JP | H 06254049 A | 9/1994 |
| JP | H 06315458 A | 11/1994 |
| JP | 200856900 A | 3/1996 |
| JP | 2008182648 A | 7/1996 |
| JP | H 07194516 A | 7/1996 |
| JP | 2009276208 A | 10/1997 |
| JP | H 10225439 A | 8/1998 |
| JP | H 11244225 A | 9/1999 |
| JP | 2001061772 A | 3/2001 |
| JP | 2001510696 A | 8/2001 |
| JP | 2002160691 A | 6/2002 |
| JP | 2002291699 A | 10/2002 |
| JP | 2003190085 A | 7/2003 |
| JP | 2005304586 | 8/2005 |
| JP | 2007111541 A | 5/2007 |
| JP | 2007252921 A | 10/2007 |
| JP | 2007313047 A | 12/2007 |
| JP | 2009505688 A | 2/2009 |
| JP | 2009101134 A | 5/2009 |
| JP | 2009530051 A | 8/2009 |
| JP | 2009201762 A | 9/2009 |
| JP | 2012245058 A | 12/2012 |
| JP | 2016174822 A | 10/2016 |
| WO | WO 2000/13569 A1 | 3/2000 |
| WO | WO 2000/33727 A1 | 6/2000 |
| WO | WO 2005/094665 A2 | 10/2005 |
| WO | WO2008/056642 A1 | 5/2008 |
| WO | WO 2009/008596 A1 | 1/2009 |
| WO | WO 2011/108157 A1 | 9/2011 |
| WO | WO 2011/114772 A1 | 9/2011 |
| WO | WO 2013/129204 A1 | 9/2013 |
| WO | WO 2019/211457 | 11/2019 |
| WO | WO 2020/178723 | 9/2020 |

OTHER PUBLICATIONS

International Search Report issued on Jan. 13, 2015 for International Application No. PCT/EP2014/073064.

International Search Report issued on Jan. 13, 2015 for International Application No. PCT/EP2014/073066.

International Search Report issued on Jan. 19, 2015 for International Application No. PCT/EP2014/073065.

International Search Report issued on Mar. 24, 2015 for International Application No. PCT/EP2014/075902.

International Search Report issued on Mar. 2, 2015 for International Application No. PCT/EP2014/077938 in 3 pages.

International Search Report issued on Mar. 24, 2015 for International Application No. PCT/EP2015/051252 in 4 pages.

Office Action issued Jun. 4, 2019 in 6 pages for Chinese Application No. 201680033009.

Search Report issued for Chinese Application No. CN 2015800056419.

Search Report issued for Chinese Application No. CN 2014800410593.

Search Report issued for Chinese Application No. CN 201480076051.

Office Action issued Sep. 4, 2017 in 7 pages for Chinese Application No. 201580005641.9.

International Search Report issued on Apr. 30, 2015 for International Application No. PCT/EP2015/051245 in 6 pages.

Anonymous: "Products I BMP-TAPPI", Jun. 30, 2013 (Jun. 30, 2013), XP055394249, Gefunden im Internet: URL: https://web.archive.org/web/20130630082009/http :// www.bmp-tappi.com:80/products [gefunden am Jul. 27, 2017].

Office Action issued Nov. 20, 2018 in 5 pages for Japanese Application No. 2017551144.

Office Action issued May 6, 2020 in 6 pages for Indian Application No. 201717043940.

(56) References Cited

OTHER PUBLICATIONS

Office Action issued Aug. 10, 2021 in 7 pages for Japanese Application No. 2020125467.

* cited by examiner

ENDOSCOPE HEAD

The present invention relates to an endoscope head comprising an endoscope head body in which at least one working channel is formed, wherein an Albarran lever capable of being pivoted is provided on the distal side of the endoscope head body.

Such an endoscope head body can be used in a duodenoscope, i.e. an endoscope for examining e.g. the esophagus or the duodenum, the bile duct, the gall bladder, the pancreatic duct, the pancreas, etc.

With the aid of the duodenoscope, it is possible to reach the duodenum through the esophagus, the stomach and the pyloric orifice.

The duodenoscope comprises (lateral) optical means (illumination means and a camera) directed to the side. This can make it difficult to introduce the duodenoscope into the esophagus and advance it therein, since forward viewing is not easily possible. Merely the stomach or the duodenum offers sufficient room to bend the distal end of the duodenoscope by about 90°, thus allowing a forward view.

Further, at the exit of the working channel, the duodenoscope comprises an Albarran lever which, by pivoting, allows the tools that are being advanced through the working channel to be selectively redirected.

After the duodenoscope has been used, it is subjected to reprocessing (cleaning and disinfection treatment). Such reprocessing has to reliably exclude the transmission of all microorganisms, such as bacteria, viruses, fungi, worms or spores. During reprocessing, the duodenoscope first undergoes manual cleaning so that organic material or chemical residues are completely removed. After cleaning, the duodenoscope is subjected to mechanical disinfection or sterilization.

It is the object of the present invention to provide an endoscope head comprising an endoscope head body which impedes the adhesion of organic material, etc.

This object is achieved by an endoscope head having an endoscope head body comprising the features of claim 1. Advantageous further developments are indicated in the dependent claims.

In the endoscope head of the present invention, at least one working channel is formed in an endoscope head body, with a pivot member actuatable from the proximal side being provided on the distal side of the endoscope head body, and an Albarran lever capable of being pivoted being provided on the distal working channel end portion. The Albarran lever is arranged at the pivot member such that it is displaceable relative to the pivot member.

The pivot member is arranged on the distal side of the endoscope head body. Thus, the Albarran lever can be separated from the pivot member and, as a consequence, from the endoscope head body. In other words, the Albarran lever and the pivot member can form separate assemblies which are detachable from each other.

Therefore, the Albarran lever can be cleaned separately from the pivot member.

Thus, with a view to enabling residue-free removal of organic material, etc., the design of the endoscope head body is rather simple. Compared to an endoscope head whose Albarran lever remains at the pivot member during cleaning, the endoscope head of the present invention has less undercuts, indentations and other locations where residues could be deposited.

It is even possible to provide the Albarran lever as an element for single use. In such a case, cleaning of the Albarran lever could be omitted. The next application of the cleaned endoscope head body will then take place with a new Albarran lever. This opens up a plurality of possibilities of designing the endoscope head body with the pivot member such that it is easy to clean and/or cost-efficient.

The Albarran lever can be detachably mountable to and demountable from the pivot member without the use of tools. For instance, the Albarran lever can be attached to the pivot member by a click-on or latching connection, by sufficiently high static friction, by means of a hook device, etc.

The Albarran lever can be detachably mountable to and demountable from the pivot member with the use of tools. For instance, the Albarran lever can be screwed to the pivot member or can be connected thereto by a splint or a pin, etc.

Further, the endoscope head can comprise a cap which can be distally slid onto the endoscope head and in which the Albarran lever is arranged such that it can be pivoted relative to the cap. The Albarran lever can be relatively displaceable at the pivot member, independently from the cap. Thus, a system of at least three separable assemblies can be formed: the endoscope head body comprising the pivot member; the Albarran lever; and the cap. Each of these assemblies can be cleaned separately.

Alternatively, the endoscope head can comprise a cap which can be distally slid onto the endoscope head and in which the Albarran lever is arranged such that it can be pivoted relative to the cap. Thus, the Albarran lever and the cap can form a common assembly which, on the distal side of the endoscope head body, is detachably mountable as a unit. The common assembly consisting of the Albarran lever and the cap can be cleaned separately from the endoscope head body. Alternatively, the common assembly consisting of the Albarran lever and the cap can be designed as an element for single use.

Thus, a variety of possibilities opens up: both the cap and the Albarran lever can, individually or as a common integrated assembly, be designed as elements for single use; alternatively, both the cap and the Albarran lever can, individually or as a common integrated assembly, be designed as elements for multiple use, which can be cleaned. Since such cleaning is performed separately from the endoscope head body and since there is a high degree of freedom with respect to the more detailed design of both the cap and the Albarran lever, individually or as a common integrated assembly, effective cleaning can be accomplished.

The proximally actuatable pivot member can form a common assembly together with a supporting member supporting the axis of the proximally actuatable pivot member. This common assembly is detachable from and mountable to the endoscope head body, wherein in the operational state, the common assembly is surrounded by the cap. Thus, even a system of four separable common assemblies can be formed: the endoscope head body comprising the pivot member; the supporting member assembly; the Albarran lever; and the cap. Each of these common assemblies can be cleaned separately.

On the other hand, the proximally actuatable pivot member can be housed in the endoscope head body together with the supporting member supporting the axis of the proximally actuatable pivot member. Thus, a construction in which only the pivot member connectable to the Albarran lever projects from the endoscope head body can be adopted. Such an endoscope head body has a compact design so that there are hardly any locations to which residues could possibly adhere.

The proximally actuatable pivot member can comprise a force receiving member into which a control wire is fittable. Thus, the pivot member can be actuated directly by the control wire.

The endoscope head body can comprise a control wire channel through which the control wire fitted into the force receiving member extends. A fitting member provided at the distal end of the control wire and fitted into the force receiving member of the pivot member can be arranged inside the endoscope head body. In this way, the distal end of the control wire is not contaminated since it is always surrounded by the outer wall of the endoscope head body. The control wire channel can be located inside the endoscope head body in such a manner that it is completely separated from and sealed against the surrounding of the endoscope head body.

Between the proximally actuatable pivot member and the Albarran lever, a sealing member can be arranged. The sealing member can, for example, be arranged on the axis of the pivot member. Thus, the pivot member and the Albarran lever are separable; however, the location where they are separated can be effectively sealed by the sealing member.

The Albarran lever can be formed as a shovel whose distal end edge can be pivoted about a pivot axis of the pivot member up to a location which, as viewed in the longitudinal direction of the endoscope head body, is provided proximally relative to the pivot axis of the pivot member. By such a design, an exit angle which by far exceeds 90 degrees can be attained for an operation member, such as a guide wire, guided in the working channel. In this way, it is much easier for the user to introduce the guide wire e.g. into the bile duct or into the pancreatic duct when the endoscope head body is positioned in the duodenum opposite the exit (papilla) of the bile duct.

The Albarran lever can be formed as a shovel whose inner surface forms an extension portion of the working channel, with the shovel inner surface being curved such that it forms a tangent from the straight working channel end portion of the endoscope head body to the curved working channel extension portion of the Albarran lever.

The shovel inner surface can be curved such that the tangent point to the straight working channel end portion of the endoscope head body is located at the proximal end edge of the shovel shape of the Albarran lever. Alternatively, the shovel inner surface can comprise a concavity and, at a proximal start segment, can turn into a straight extension portion in such a manner that the tangent point to the straight extension portion is located in the shovel shape of the Albarran lever at a distance to the proximal end edge of the shovel shape of the Albarran lever.

In this way, a smooth transition from the straight working channel end portion of the endoscope head body to the curved working channel extension portion of the Albarran lever is enabled so that an operation member, such as a guide wire, a tool, etc., guided in the working channel can gently be pushed out of the endoscope head body without a strong increase in resistance.

The above discussed aspects of the present invention can be combined appropriately.

Embodiments of the present invention will be described below in detail with reference to the drawings.

Embodiment 1

A first embodiment of the present invention will be described below with reference to FIGS. 1 to 9.

Figure 1:
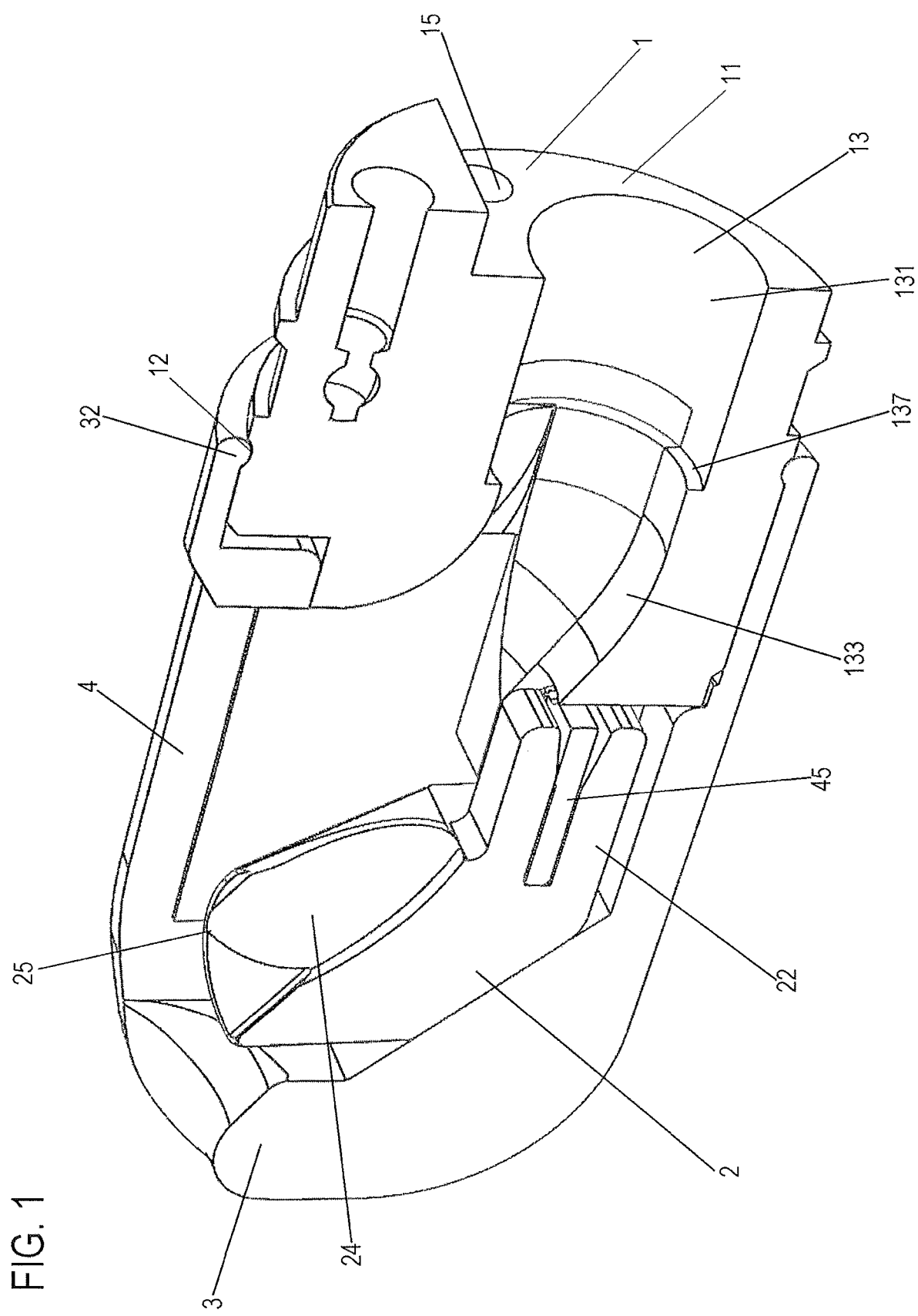
FIG. 1 shows a partly cut-open perspective view of an endoscope head of a first embodiment according to the present invention in an assembled state.
Figure 2:
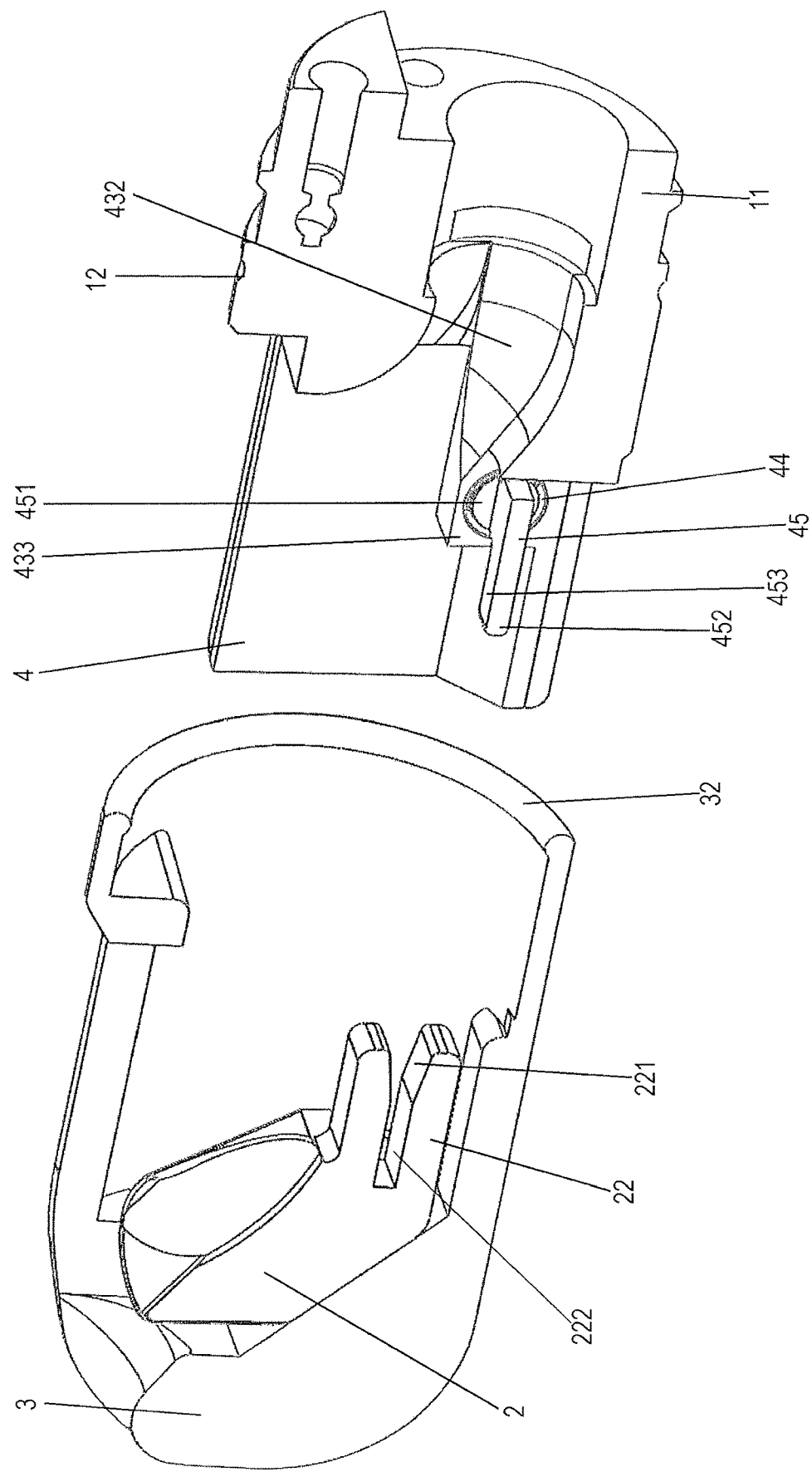
FIG. 2 shows a partly cut-open perspective view of the endoscope head of the first embodiment according to the present invention in an extracted state.

Each of FIGS. 1 and 2 shows a perspective view of a first embodiment of an endoscope head according to the invention.

In particular, FIGS. 1 and 2 show this endoscope head from the side in a partly cut-open perspective view, with the left side of the drawing pointing in the insertion direction of the endoscope head.

An endoscope head 1 comprises an endoscope head body 11 having an Albarran lever 2 at its distal end, the Albarran lever 2 being surrounded by a cap 3. The Albarran lever 2 is arranged such that it can be pivoted relative to the endoscope head body 11 and, for this purpose, is pivoted by means of a pivot lever 45. The pivot lever 45 is rotatably supported at a side supporting member (supporting member) 4. The Albarran lever 2 can be slid away from the pivot lever 45.

FIG. 1 shows a view in which the Albarran lever 2 and the pivot lever 45 are in an assembled state. FIG. 2 shows a view in which the pivot lever 45 has been pulled out of the Albarran lever 2 (extracted state). In the following, the individual members of the endoscope head 1 will be discussed in detail.

Endoscope Head Body 11

The endoscope head body 11 is designed as a cylindrical body and comprises a working channel 13 and a control wire channel 15, each extending along the longitudinal direction of the endoscope head body 11 and in parallel to each other. The control wire channel 15 guides a subsequently described control wire for operating the Albarran lever 2. The working channel 13 guides microtools for examining, for example, the esophagus, the duodenum, the bile duct, the gall bladder, the pancreatic duct, the pancreas, etc.

On its outer circumferential surface, the endoscope head body 11 comprises a groove 12 extending in parallel to the proximal end side of the endoscope head body 11, the groove 12 serving as a locking groove for the cap 3.

Figure 4:
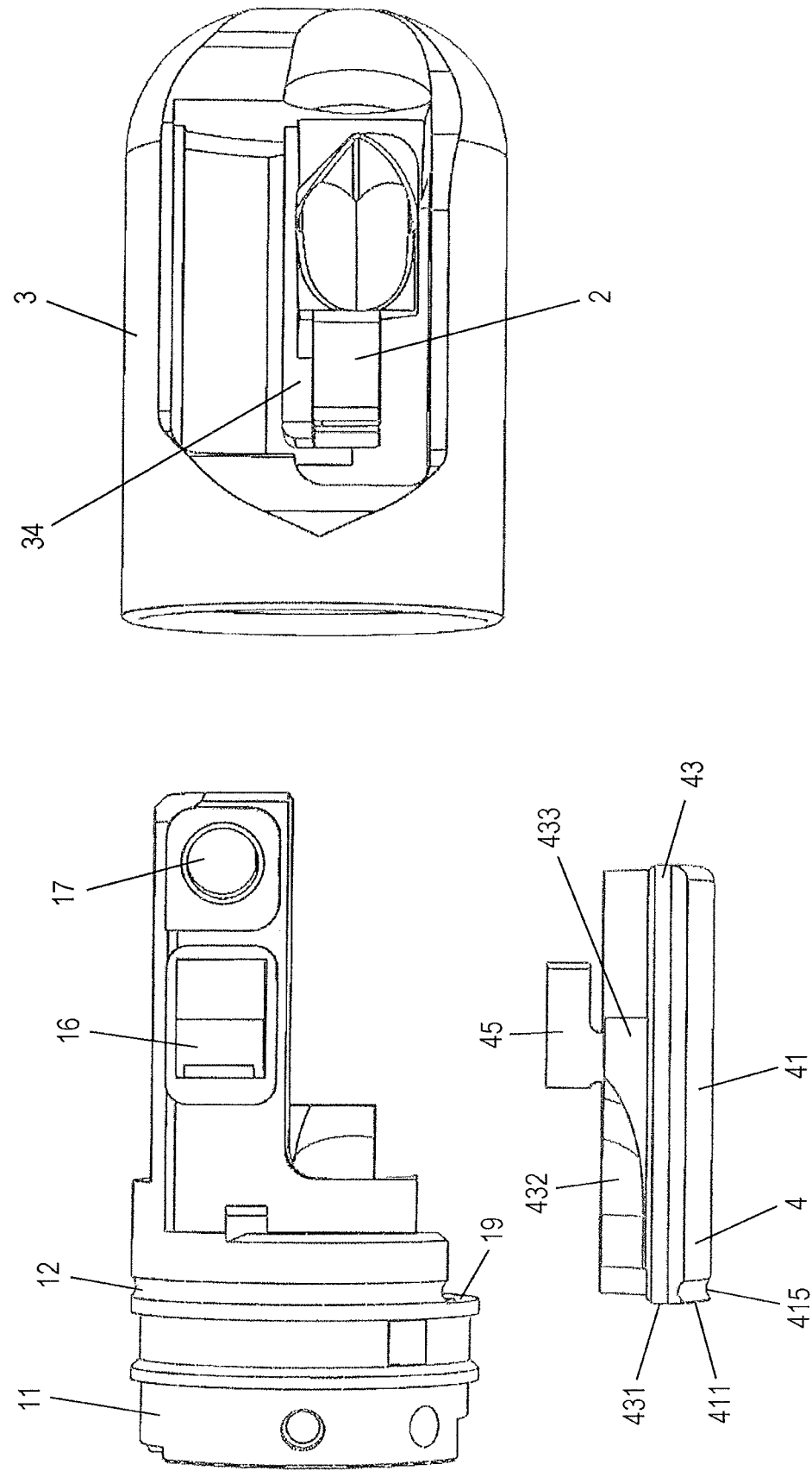
FIG. 4 shows a perspective view of the endoscope head of the first embodiment according to the present invention, where a side supporting member is detachable.

On its distal side, the endoscope head body 11 comprises an extension portion at which a camera 16 and an illumination means 17 are provided in the known manner, as is shown, for example, in FIG. 4.

At its proximal end, the endoscope head body 11 comprises a cylindrical opening having an inner surface 131 for the working channel 13. In the cylindrical opening, an actual working channel member (not shown) formed as a flexible tube member is arranged. When inserted into the endoscope head body 11, the working channel member extends in the proximal direction and serves for guiding the microtools.

At the distal end of the endoscope head body 11, a curved portion 133 is provided, as is shown in FIG. 1. The working channel member (not shown) is inserted into the opening having the inner surface 131 to such an extent that it abuts on a radial contact surface 137 on the proximal side of the curved portion 133. Thus, the working channel 13 comprises the curved portion 133 at which the direction of the working channel 13 starts changing from an approximate straight line to a bending.

The curved portion 133 extends in a curved manner to the distal side towards the prolonged center axis of the opening having the inner surface 131 and, in doing so, acts together with a curve-shaped member 432 described later, see FIG. 2. The Albarran lever 2 capable of being pivoted relative to the endoscope head body 11 is seated at the distal exit of the working channel 13. Thus, beyond the curved portion 133, the working channel 13 extends further towards the Albarran lever 2 in the distal direction.

Albarran Lever 2

The Albarran lever 2 comprises an Albarran lever main body 21 which, on the front (proximal) side in FIG. 1, comprises an Albarran lever fork portion (yoke) 22 into which the pivot lever 45 is inserted for performing the pivoting operation of the Albarran lever 2. As shown in FIG. 2, the fork portion 22 comprises two parallel contact surfaces (in FIG. 2, only the lower contact surface is shown), each of which ends in an insertion surface 221 towards the proximal side. The insertion surface 221 is a surface inclined towards the proximal side. On the distal side, the insertion surface 221 turns into the contact surface 222. The insertion surfaces 221 (in FIG. 2, only the lower insertion surface 221 is shown) serve for inserting the pivot lever 45 into the fork portion 22. In the inserted state, the pivot lever 45 is provided in the fork portion 22 such that it is in contact with at least one of the contact surfaces 222. The pivot lever 45 comprises a pivot lever arm 452 inserted into the fork portion 22. The arm 452 of the pivot lever 45 is formed cuboid-like and comprises an upper and a lower insertion surface 453, as shown in FIG. 2. The upper and lower insertion surfaces 453 are opposite to each other and extend in the longitudinal direction of the endoscope head body 11. Only the upper insertion surface 453 is shown in FIG. 2. Preferably, the thickness of the arm 452, that is the distance between the upper and lower insertion surfaces 453 facing away from each other, is slightly smaller than the distance between the parallel contact surfaces 222 of the fork portion 22 of the Albarran lever 2. Therefore, the pivot lever 45 can be inserted into the fork portion 22 of the Albarran lever 2 with ease.

The pivot lever arm 452 comprises a rotation shaft 451 which is described hereinafter and about which the pivot lever arm 452 can pivot or rotate.

The Albarran lever 2 comprises a working channel surface 24 forming an extension portion of the working channel 13 when the Albarran lever 2 is positioned relative to the endoscope head body 11, as shown in FIG. 1. The working channel surface 24 comprises a curvature provided in the extension direction of the endoscope head 1 and ending at a distal end 25 of the working channel surface 24. The working channel surface 24 is curved inwardly, i.e. it is concave.

A tool, such as a guide wire, guided through the working channel 13 is lifted up by the curved portion 133 and comes into contact with the working channel surface 24 of the Albarran lever 2 when being further advanced in the proximal direction.

The Albarran lever 2 can be pivoted relative to the endoscope head body 11. Here, the fulcrum (rotation axis) and the physical design of the Albarran lever 2 are selected such that in the swung-out position of the Albarran lever 2, the distal end 25 of the working channel surface 24 is located proximally relative to the fulcrum of the Albarran lever 2, when viewed in the longitudinal direction of the endoscope head body 11.

Cap 3

The cap 3 is formed as a cylinder provided with a bottom. The bottom of the cap 3 is located on the distal side thereof. In an application state, the cap 3 is placed on the endoscope head body 11. In the area of the bottom, the outside of the cap 3 is rounded such that the requirements for inserting the endoscope head 1 into an object to be examined are fulfilled.

Figure 3:
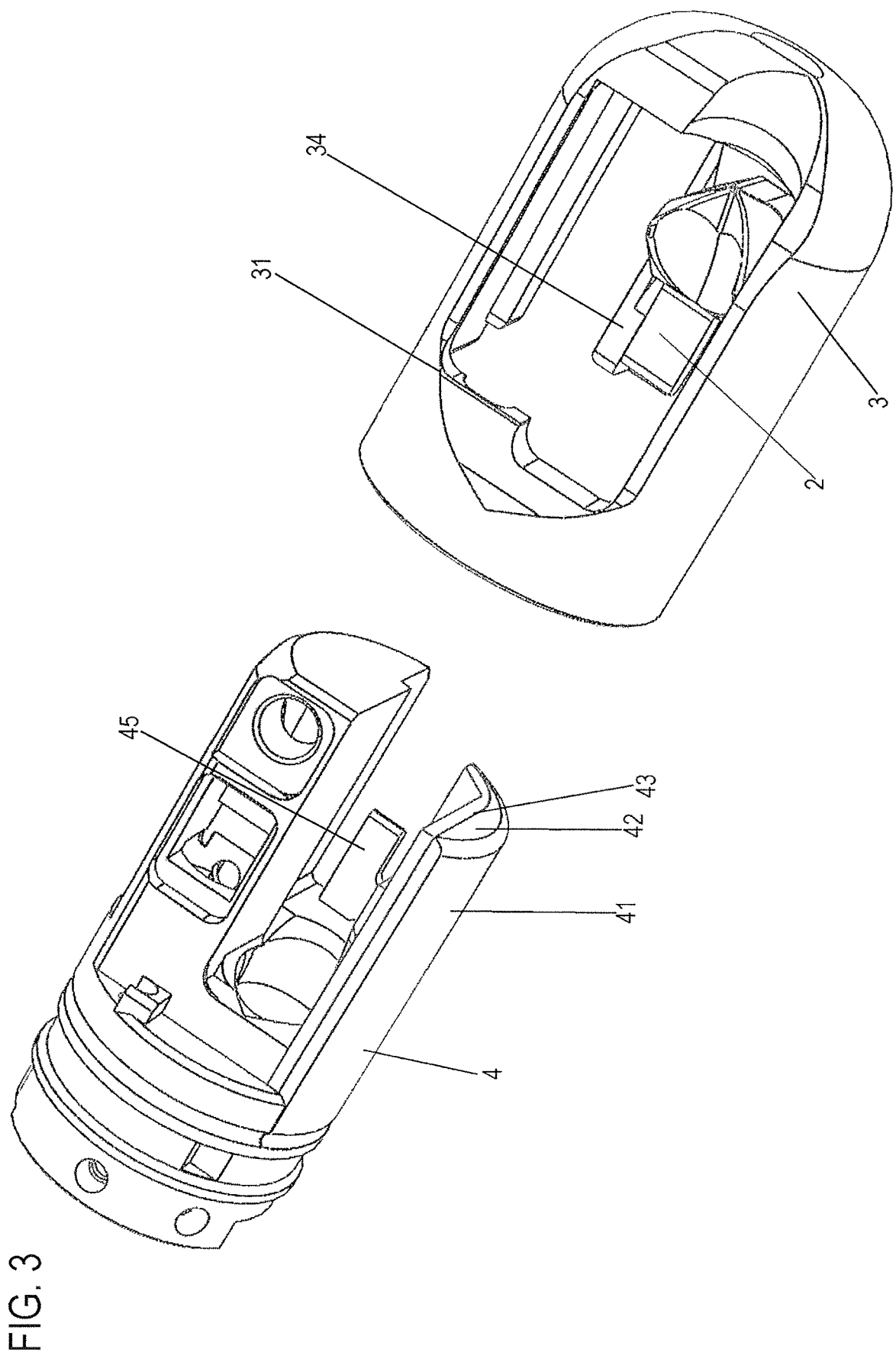
FIG. 3 shows a perspective view of the endoscope head of the first embodiment according to the present invention in an extracted state viewed from above.

The cap 3 comprises an opening 31 which, in FIG. 3, faces upwards (cf. FIG. 3). When using the endoscope head 1, the opening 31 of the cap 3 forms an open lateral window for the tools guided through the working channel 13.

At its proximal end, the cap 3 has a locking nose 32 which projects inwardly along the overall circumference of the cap 3 and which can have a round or curved shape or any other shape. This locking nose 32 can be locked in the groove 12 of the endoscope head body 11 when the cap 3 is placed on the endoscope head body 11. The groove 12 comprises a shape corresponding to the shape of the locking nose 32.

Figure 5:
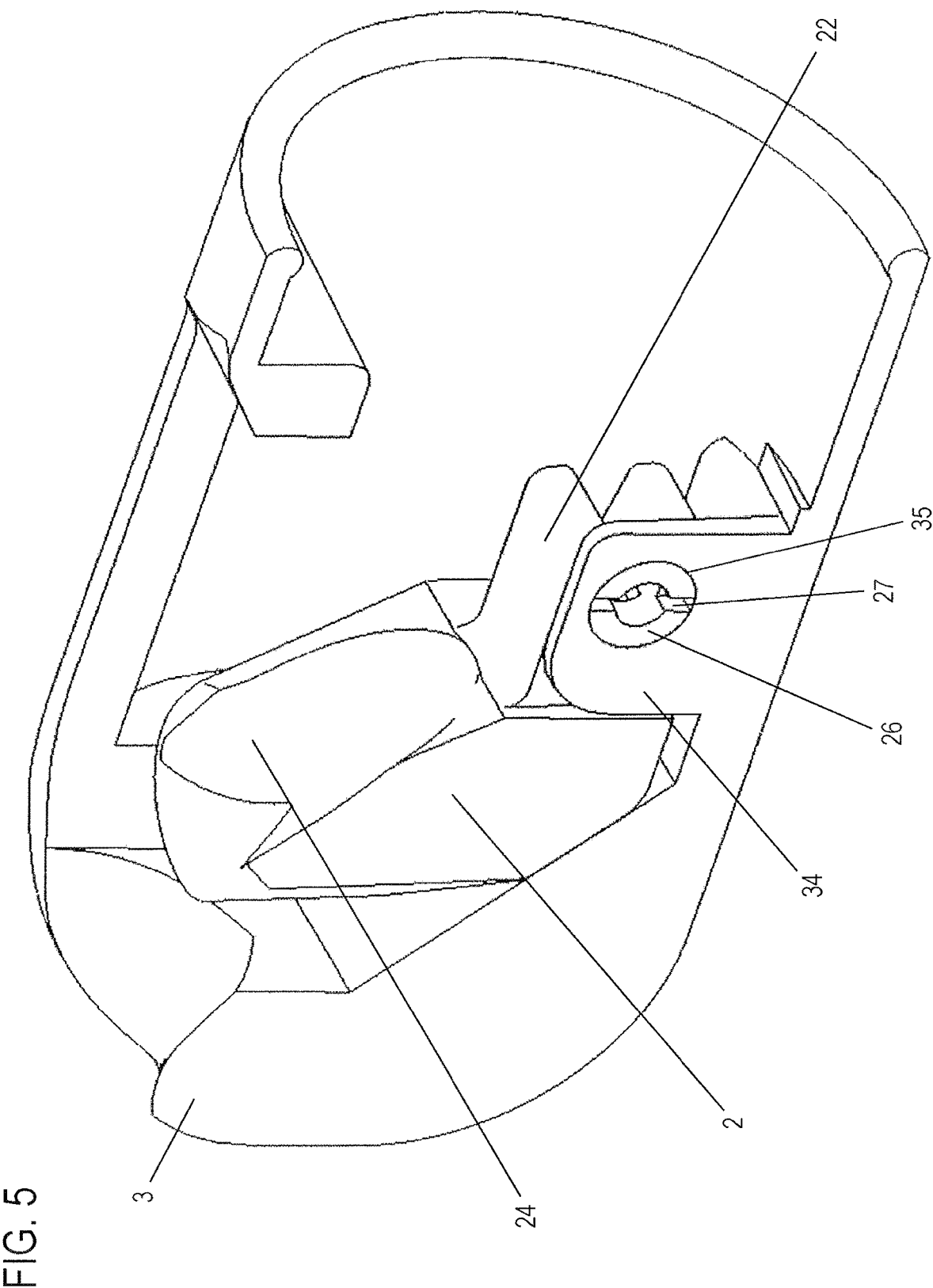
FIG. 5 shows a perspective view of a cap of the endoscope head of the first embodiment according to the present invention.

In the inside thereof, the cap 3 comprises a lever holder 34 opposite to the opening 31, the lever holder 34 being provided as a projection protruding from the inner circumferential surface of the cap 3, see FIGS. 3 to 5.

The lever holder 34 comprises a bore 35 extending perpendicularly with respect to the longitudinal extension of the cap 3 and having a pivot projection 26 of the Albarran lever 2 inserted therein, as shown in FIG. 5. In the representations of FIGS. 1 and 2, the pivot projection 26 of the Albarran lever 2 is on the side of the Albarran lever 2 facing towards the viewer, but has been omitted in these Figures for the sake of simplicity and due to the position of the section of the sectional view. The pivot projection 26 has a cylindrical shape and extends laterally from the fork portion 22 of the Albarran lever 2.

The outer diameter of the pivot projection 26 is selected such that the pivot projection 26 is easily rotatable in the bore 35 of the lever holder 34. For instance, the outer diameter of the pivot projection 26 can be slightly smaller than the inner diameter of the bore 35.

As shown in FIG. 5, on the side opposite to the fork portion 22, the pivot projection 26 can comprise a slit 27 extending in the longitudinal direction of the pivot projection 26. The slit 27 facilitates insertion of the pivot projection 26 into the bore 35 of the lever holder 34 since the pivot projection 26 can be slightly compressed inwardly in the area of the slit 27. Alternatively, the pivot projection 26 can be formed as a solid cylindrical projection.

When the cap 3 is placed on the endoscope head body 11, the center axis of the pivot projection 26 of the Albarran lever 2 is aligned to the center axis of the rotation shaft 451 of the arm 452. This means that both center axes are on the same line.

Thus, the Albarran lever 2 is integrated into the cap 3, and both the Albarran lever 2 and the cap 3 form a common assembly and are movable relative to the endoscope head body 11 as a unit.

The Albarran lever 2 pivots about the axis of the pivot projection 26 (axis of the bore 35) towards the opening 31 of the cap 3.

Side Supporting Member 4

The side supporting member 4 rotatably supports the pivot lever 45. The side supporting member 4 comprises an inner member 43 which is a plate member approximately in the shape of a letter L in cross-section, see FIG. 3. The inner member 43 serves for supporting the pivot lever 45, with the pivot lever 45 being rotatably supported in the inner member 43. More precisely, when assembled to the endoscope head body 11, the inner member 43 extends in parallel to the longitudinal direction of the endoscope head body 11. The inner member 43 has the shape of an angled plate, wherein the angulation line extends in parallel to the longitudinal direction of the endoscope head body 11 and separates the plate shape of the inner member 43 into a larger plate portion (the upper plate portion in FIG. 3) and a smaller plate portion (the lower plate portion in FIG. 3), the larger plate portion forming the long side of the L-shape and the smaller plate portion forming the base (foot) of the L-shape. In the center portion of the inner member 43, as seen in the longitudinal direction, there is provided a material reinforcement portion 433 formed integrally with both the upper, larger plate portion and the lower, smaller plate portion. A receiving bore 44 extends through this reinforcement portion 433 perpendicularly with respect to the extension direction of the inner member 43. The receiving bore 44 serves as a bearing for the shaft body (rotation axis) 451 of the pivot lever 45. The cylindrical shaft body 451 of the pivot lever 45 is inserted into the receiving bore 44 of the reinforcement portion 433.

The outer diameter of the shaft body 451 is selected such that the shaft body 451 is easily rotatable in the receiving bore 44 of the reinforcement portion 433. For instance, the outer diameter of the shaft body 451 can be slightly smaller than the inner diameter of the receiving bore 44.

On the proximal side of the reinforcement portion 433, the inner member 43 has a curve-shaped member 432 forming a part of the working channel 13 when the inner member 43 is assembled to the endoscope head body 11, see FIG. 2. More precisely, the curve-shaped member 432 and the curved portion 133 cooperate to form the bending (curvature) of the working channel, as described above.

The inner member 43 has a flat proximal end face 431.

Further, the side supporting member 4 comprises an outer member 41 forming the radial outer side of the side supporting member 4. The outer member 41 serves as a cover of the side supporting member 4 and has an outwardly bent (convex) shape, as shown in FIG. 3. In other words, the outer member 41 is formed by a bent plate member having a constant wall thickness and the cap 3 can be attached to the outer surface of the outer member 41.

The bent plate member of the outer member 41 has a curved inner surface facing the inner member 43. Thus, the inner surface of the outer member 41 is concave. In the developed view, the outer member 41 has a rectangular shape. At the end surfaces extending in the longitudinal direction, the outer member 41 is in contact with the inner member 43. More precisely, when looking at FIG. 3, an upper, longitudinally extending end surface of the outer member 41 is in contact with the upper, longitudinally extending end surface of the upper (larger) plate portion of the inner member 43; and a lower, longitudinally extending end surface of the outer member 41 is in contact with a lower, longitudinally extending end surface of the base (lower, smaller plate portion) of the inner member 43, the latter end surface extending away from the upper (larger) plate portion of the inner member 43. Thus, between the outer member 41 and the inner member 43, a space or gap 42 is formed, as shown in FIG. 3.

On the proximal side, the outer circumferential surface of the outer member 41 is provided with a groove 415 extending in the circumferential direction. Similarly as the groove 12 of the endoscope head body 11, the groove 415 is adapted to the shape of the nose 32 of the cap 3 and, together with the groove 12, serves for allowing locking and holding of the cap 3.

The outer member 41 has a flat proximal end face 411.

The side supporting member 4 is arranged at the endoscope head body 11 in such a manner that the proximal end faces 411 and 431 of the outer member 41 and the inner member 43 are attached to a distally facing attachment surface 19 of the endoscope head body 11 e.g. by gluing. Thus, the endoscope head body 11 and the side supporting member 4 can form a common assembly. The side supporting member 4 is arranged at the attachment surface 19 in such a manner that the distal end of the control wire channel 15 opens into the gap 42.

Figure 6:
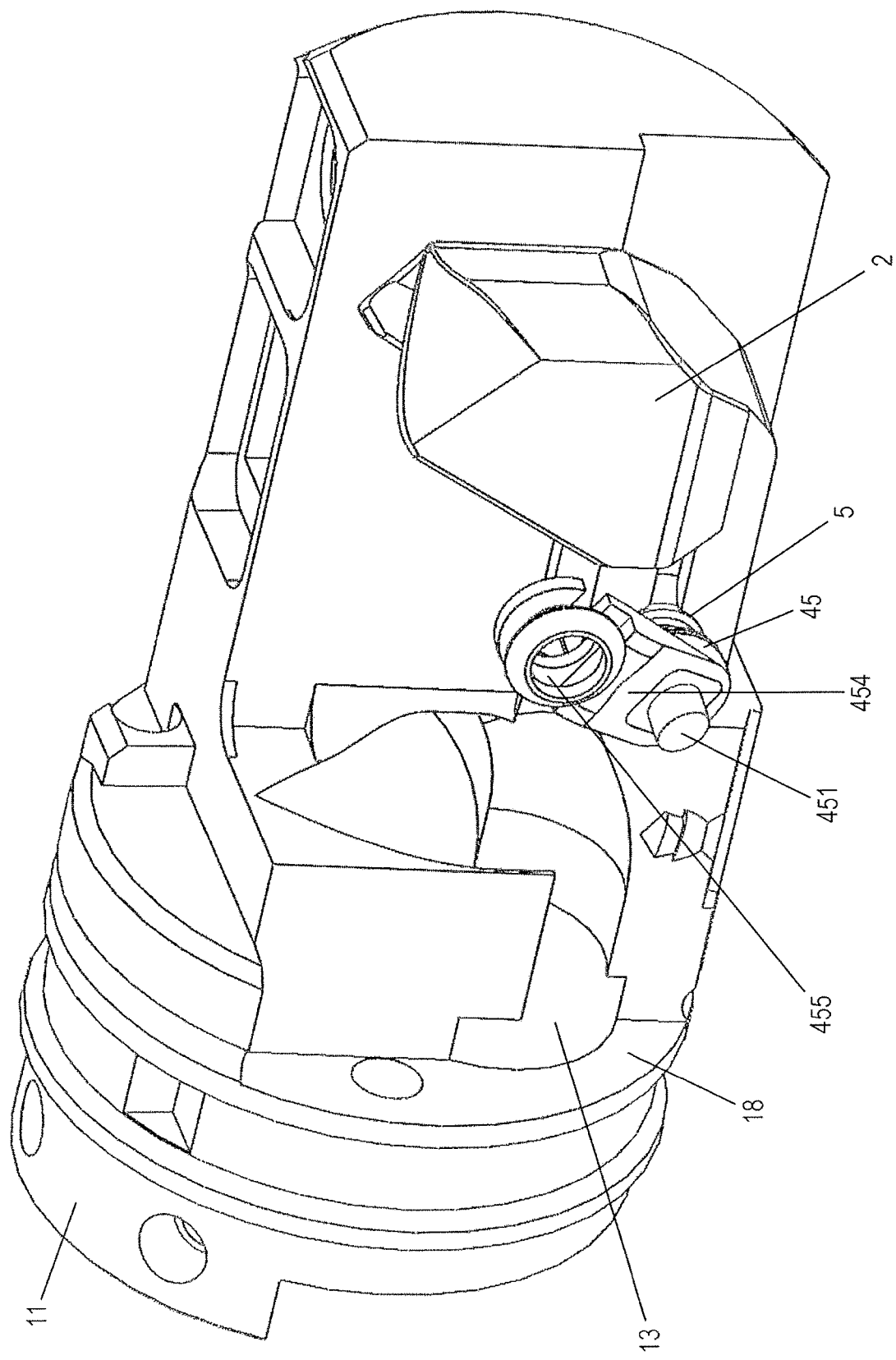
FIG. 6 shows a perspective view of the endoscope head of the first embodiment according to the present invention from the back.

On the side of the pivot lever 45 opposite to the arm 452, an activation lever 454 is arranged at the cylindrical shaft body 451 of the pivot lever 45. The activation lever 454 can be mounted on the cylindrical shaft body 451 of the pivot lever 45 in a form-fitting manner, as shown in FIG. 6. Other ways of attaching the activation lever 454 to the cylindrical shaft body 451 of the pivot lever 45 are possible. The activation lever 454 can, for example, be glued onto the end of the cylindrical shaft body 451 which is opposite to the arm 452. Here, it is noted that, for the sake of simplicity, the outer member 41 and the inner member 43 have been omitted in FIG. 6. The activation lever 454 is arranged in the gap 42 between the outer member 41 and the inner member 43. The gap 42 is a closed space defined between the outer member 41, the inner member 43, the attachment surface 19, and a distal cover not shown in the Figures. The distal cover sealingly closes the gap 42 on the distal side of the outer member 41 and the inner member 43.

On its side opposite to the shaft body 451, the activation lever 454 comprises a control wire barrel receiving member 455 into which a barrel of a control wire (not shown) is inserted. The control wire is activated from the proximal side of the endoscope head 1, for example by a control member, such as a joystick.

When the control wire is pulled by the control member, the activation lever 454 is pivoted (rotated) about its fulcrum formed in the shaft body 451. The control wire proximally extends from the barrel inserted into the control wire barrel receiving member 455 through the gap 42 between the outer member 41 and the inner member 43 into the control wire channel 15 of the endoscope head body 11, and from there further through a catheter of the endoscope to the control member. The control wire barrel receiving member 455 forms a force receiving member for receiving the force applied to the control wire and transmitting it to the pivot lever 45.

At the outer circumference of the cylindrical shaft body 451, at least one sealing ring 5 is arranged as a sealing member between the cylindrical shaft body 451 and the receiving bore 44 of the reinforcement portion 433. The sealing ring 5 is shown in FIG. 6. The sealing ring 5 has the function to seal between the pivot member 45 and the Albarran lever 2. In other words, the sealing ring 5 seals the gap 42.

Application of the Embodiment

Figure 7:
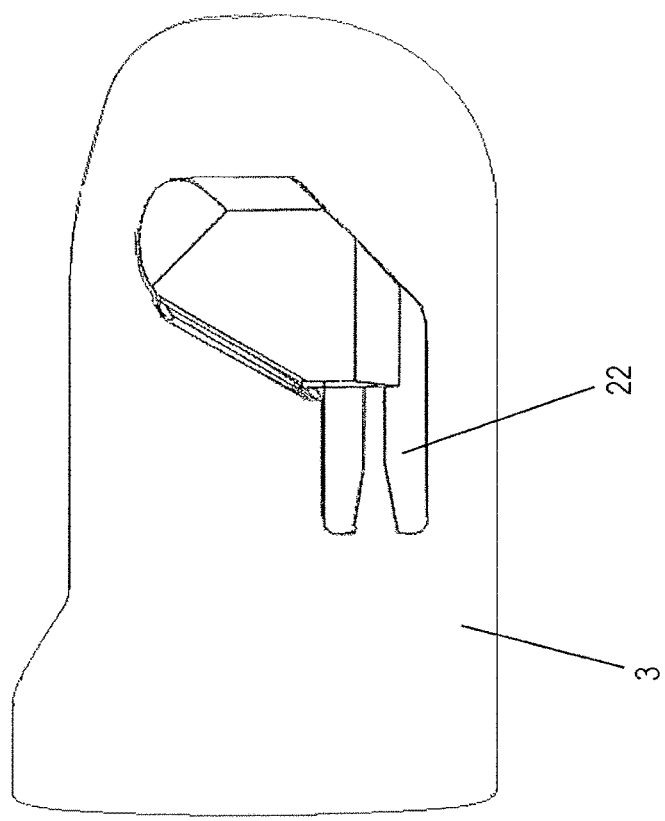
FIG. 7 shows a perspective top view of the endoscope head of the first embodiment according to the present invention, with the cap being detached.
Figure 7:
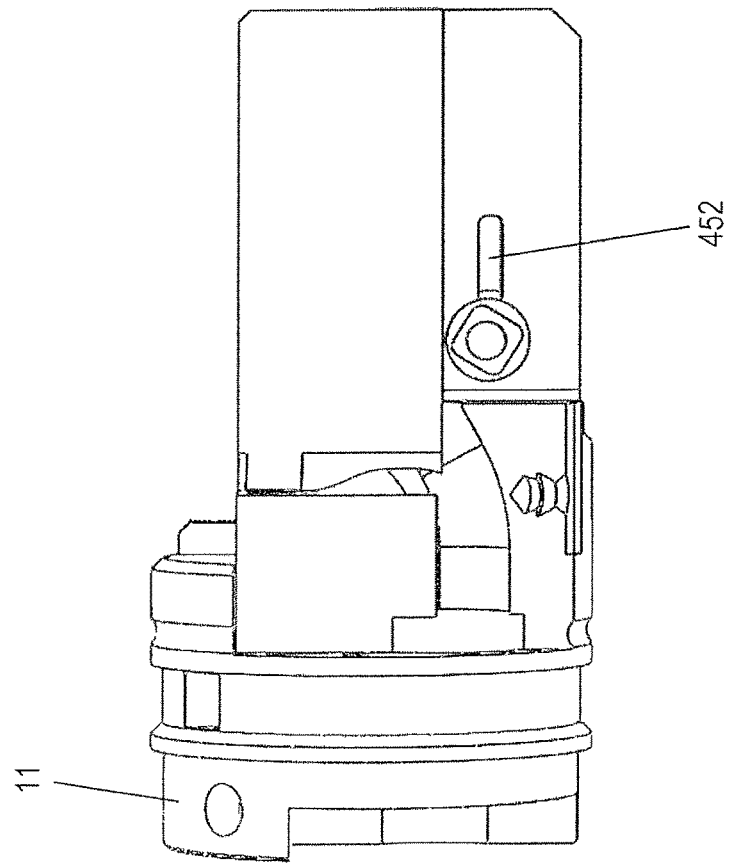
Figure 8:
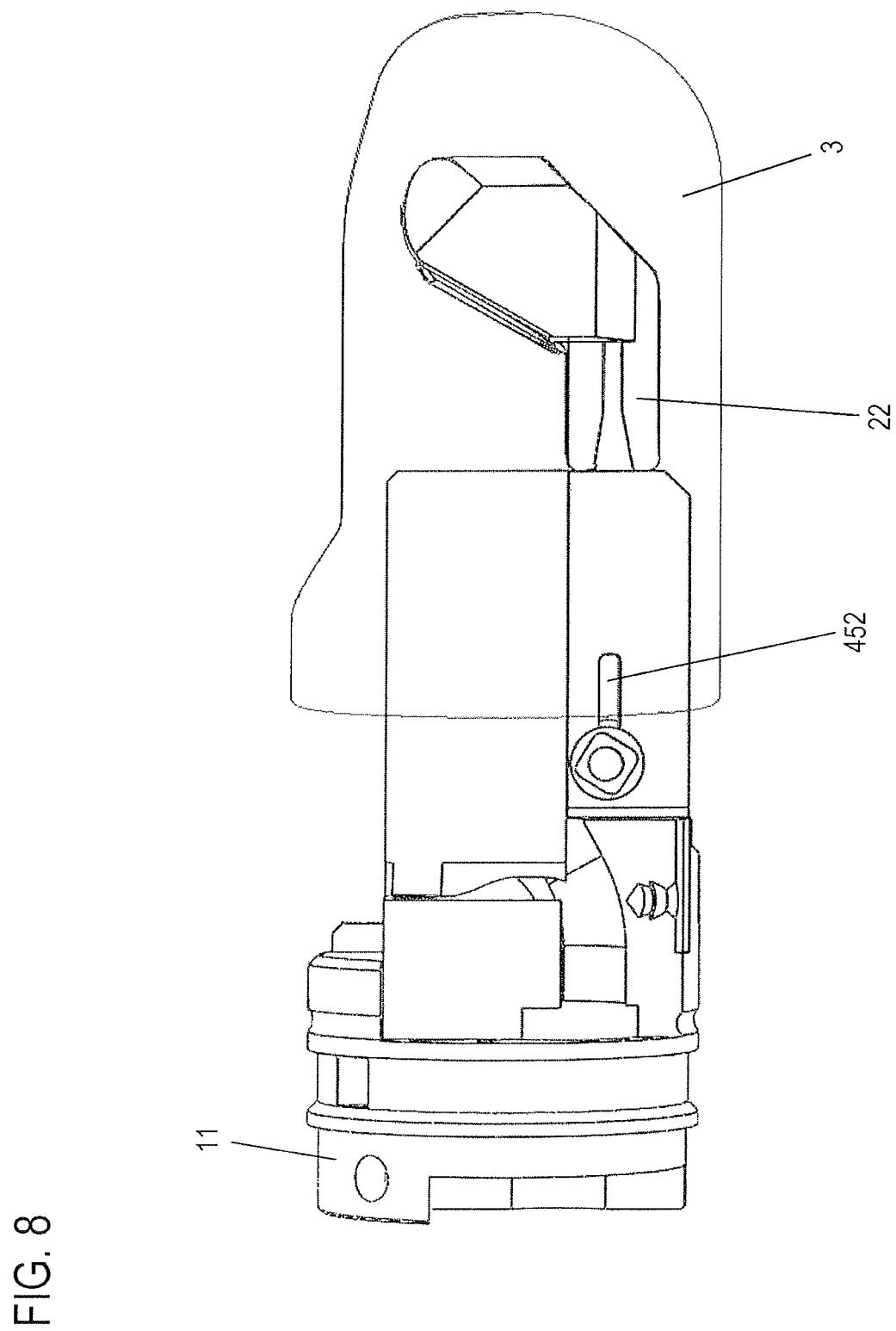
FIG. 8 shows a perspective top view of the endoscope head of the first embodiment according to the present invention in an intermediate position in which the cap is being slid onto the endoscope head.
Figure 9:
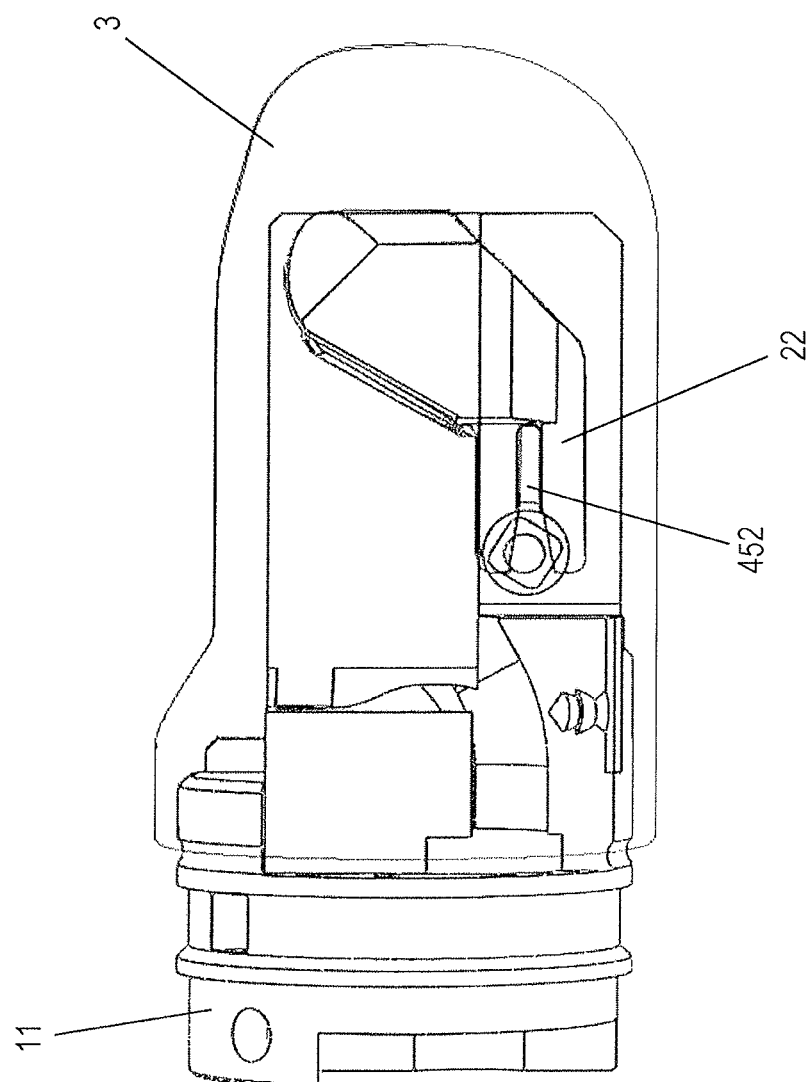
FIG. 9 shows a perspective top view of the endoscope head of the first embodiment according to the present invention, with the cap being placed on the endoscope head.

As discussed above, the cap 3 and the Albarran lever 2 form a common assembly which is separate and separable from the assembly formed by the endoscope head body 11 and the side supporting member 4. FIGS. 7 to 9 schematically show how the cap 3 is placed on the endoscope head body 11. For the sake of better illustration, the cap 3 is shown transparently.

FIG. 7 shows a perspective top view of the endoscope head in a situation where the cap 3 is separated from the endoscope head body 11 and the side supporting member 4. The cap 3 is rotated by the user such that the fork portion 22 of the Albarran lever 2 is directed towards and aligned with the distally extending arm 452. For facilitating the alignment, the cap 3 and the endoscope head body 11 can, e.g., be provided with a marking provided at the respective outer surface. In this relative position, the cap 3 is slid in the proximal direction onto the endoscope head body 11 and, thus, also the fork portion 22 of the Albarran lever 2 is slid onto the arm 452, see FIGS. 8 and 9, until the nose 32 of the cap 3 is locked at the groove 12/415. More precisely, the arm 452 is inserted into the fork portion 22 in such a manner that its upwards and downwards directed insertion surfaces 453 face the contact surfaces 222 of the fork portion 22. According to the present invention, in the position resulting from locking the cap 3 on the endoscope head body 11, the rotation shaft 451 and the pivot projection 26 are aligned axially.

When the control wire is pulled on the proximal side, the activation lever 454 is pivoted about its fulcrum formed in the shaft body 451. Analogously, the shaft body 451 and, thus, the arm 452 of the pivot lever 45 rotate (pivot). In turn, the rotation of the pivot lever 45 seated in the fork portion 22 causes the pivoting operation of the Albarran lever 2.

Advantages of the Embodiment

Since the cap 3 and the Albarran lever 2 form a common assembly which can be separated from the common assembly consisting of the endoscope head body 11 and the side supporting member 4, the cap 3 and the Albarran lever 2 can be designed as an assembly for single use.

The common assembly consisting of the endoscope head body 11 and the side supporting member 4 can easily be cleaned and reprocessed. The common assembly formed by the endoscope head body 11 and the side supporting member 4 of the present invention does not have any undercuts or locations difficult to reach at the Albarran lever itself or at the Albarran lever mounted to the endoscope head body. The rinsing liquid for cleaning can easily flow around the common assembly consisting of the endoscope head body 11 and the side supporting member 4 and can remove foreign particles therefrom.

When reusing the endoscope head 1, simply a new common assembly consisting of the cap 3 and the Albarran lever 2 is placed on the endoscope head 1. In this way, contaminations of the endoscope head 1 can be prevented even better than in the prior art. With such an endoscope head 1 according to the present invention, patients are better protected against germs which adhered to the endoscope head during previous applications.

Embodiment 2

A second embodiment of the present invention will be described below with reference to FIGS. 10 to 15.

Figure 10:
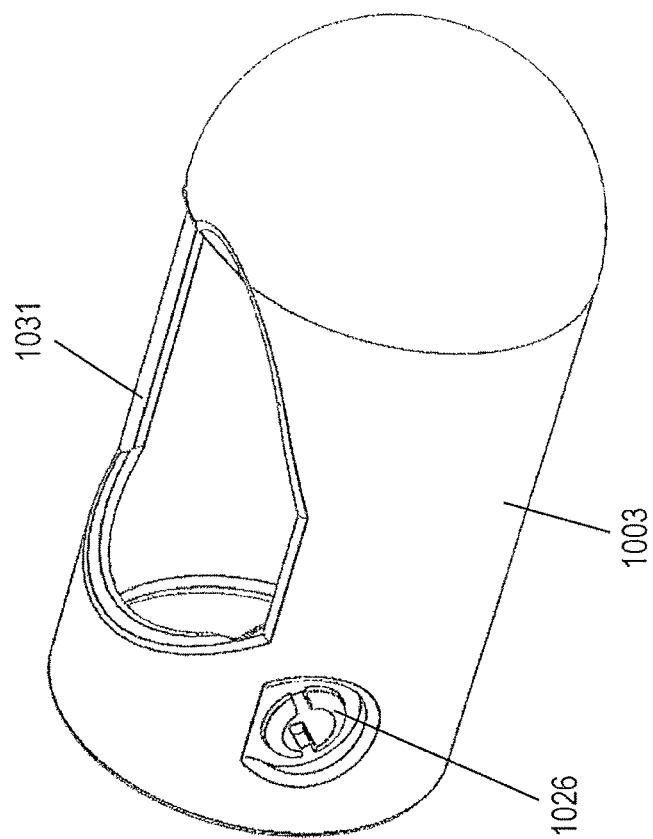
FIG. 10 shows a perspective side view of an endoscope head of a second embodiment according to the present invention.
Figure 10:
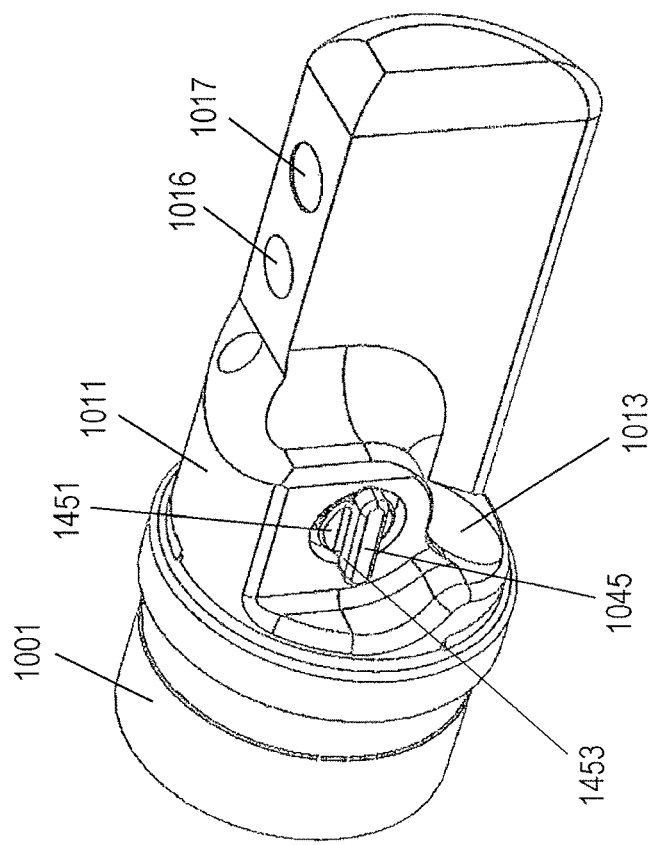
Figure 11:
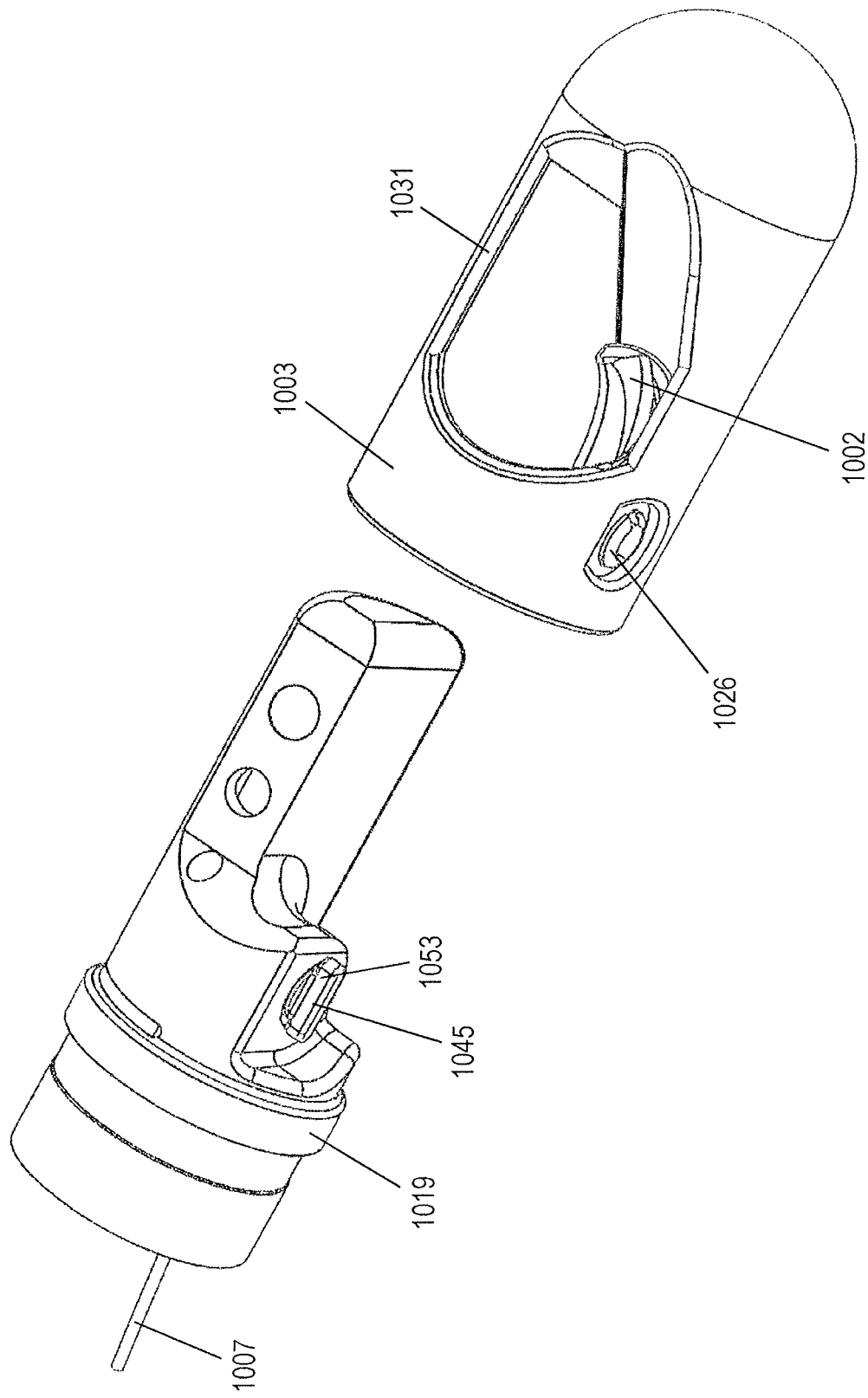
FIG. 11 shows a perspective top view of the endoscope head of the second embodiment according to the present invention.
Figure 12:
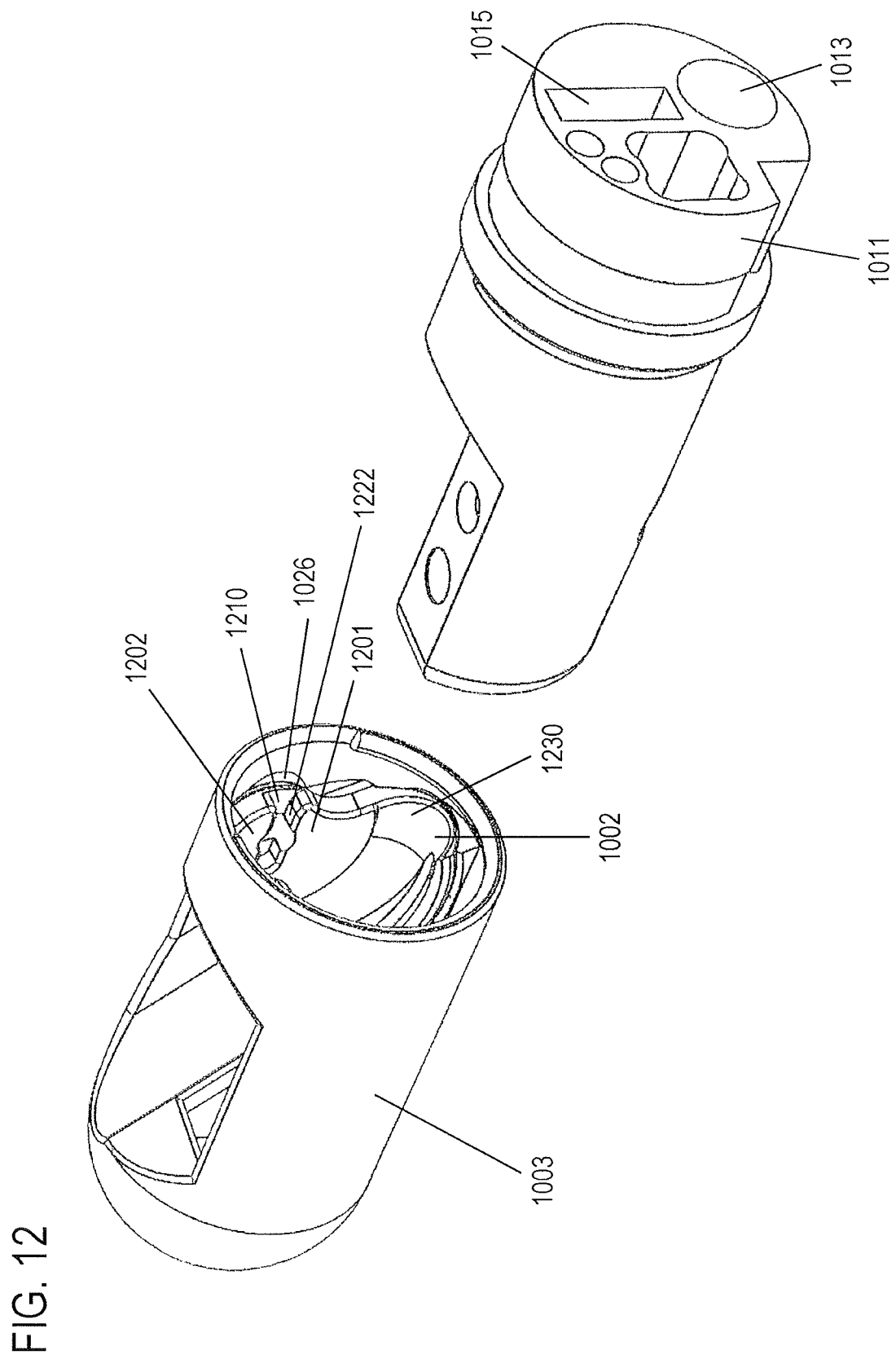
FIG. 12 shows a perspective view of the endoscope head of the second embodiment according to the present invention, seen from the proximal side.

FIGS. 10 to 12 show perspective views of the endoscope head body of the second embodiment. Those elements of the second embodiment which are the same as the respective elements of the first embodiment are not further discussed and, if they are shown, have been provided with the same reference signs.

In the following, mainly the differences between the first and second embodiment will be described. Contrary to the first embodiment, the pivot lever according to the second embodiment is not provided in a supporting member separable from the endoscope head body, but is integrated in the endoscope head body. The Albarran lever of the second embodiment is different from the Albarran lever of the first embodiment.

An endoscope head 1001 comprises an endoscope head body 1011 having an Albarran lever 1002 arranged at the distal end thereof, the Albarran lever 1002 being surrounded by a cap 1003. The Albarran lever 1002 is arranged such that it can be pivoted relative to the endoscope head body 1011 and is pivoted by a pivot lever 1045. The pivot lever 1045 is rotatably supported at the endoscope head body 1011. The Albarran lever 1002 can be slid away from the pivot lever 1045.

Thus, the endoscope head 1001 comprises two common assemblies: the endoscope head body 1011 with the pivot lever 1045 installed therein as a first common assembly, and the cap 1003 with the Albarran lever 1002 installed therein as a second common assembly. In the following, these two common assemblies will be described in greater detail.

Endoscope head body 1011 with pivot lever 1045 installed therein

The endoscope head body 1011 is designed as a cylindrical body and comprises a working channel 1013 and a control wire channel 1015, each extending along the longitudinal direction of the endoscope head body 1011 and in parallel to each other. The control wire channel 1015 guides a control wire 1007 for operating the Albarran lever 1002. The working channel 1013 guides the microtools for the examinations. On its distal side, the endoscope head body 1011 comprises an extension portion at which a camera 1016 and an illumination means 1017 are provided in the known manner.

Figure 13:
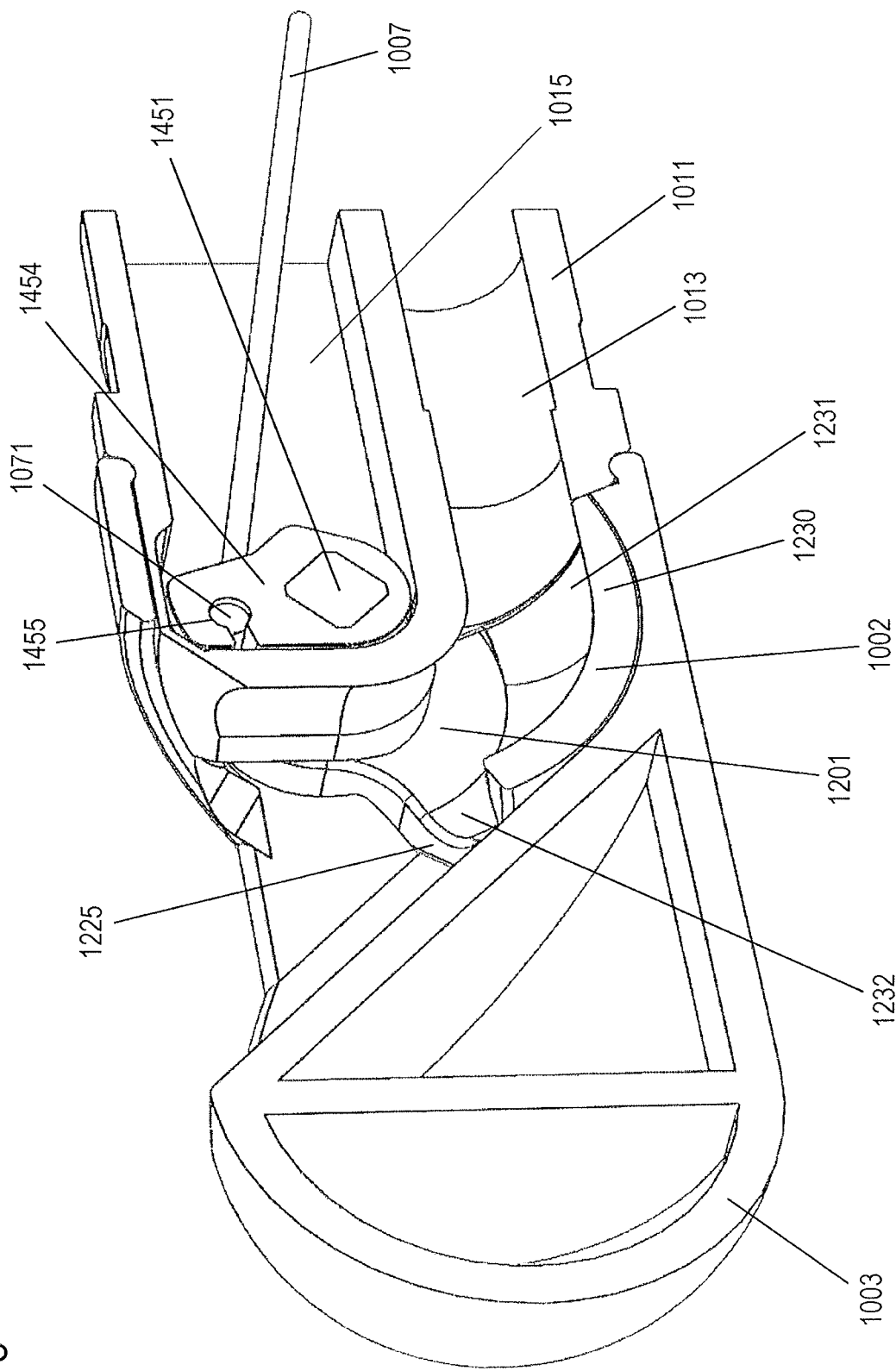
FIG. 13 shows a cut-open perspective view of the endoscope head of the second embodiment according to the present invention in a state in which the Albarran lever is in a rest position.
Figure 14:
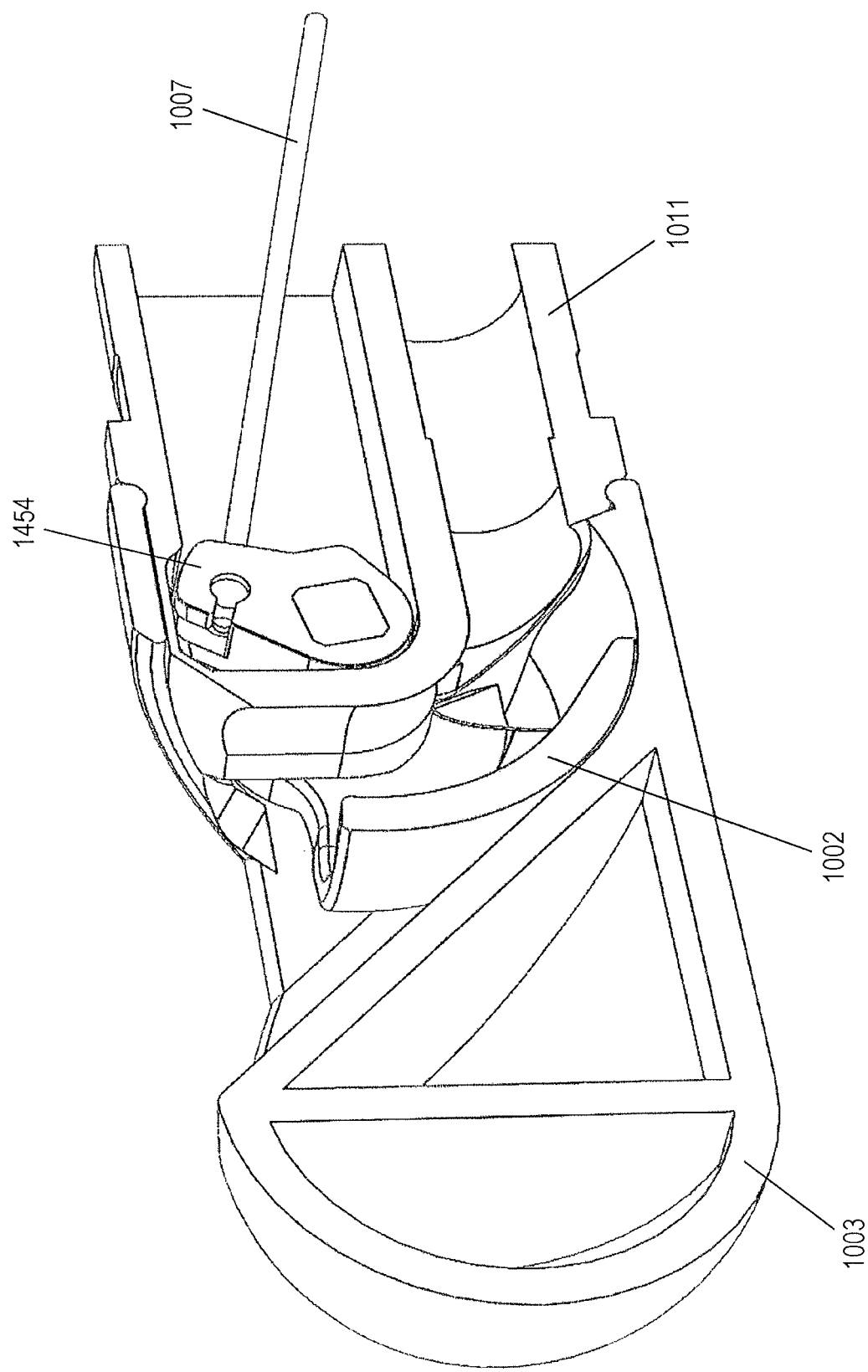
FIG. 14 shows a cut-open perspective view of the endoscope head of the second embodiment according to the present invention in a state in which the Albarran lever is in an intermediate position.
Figure 15:
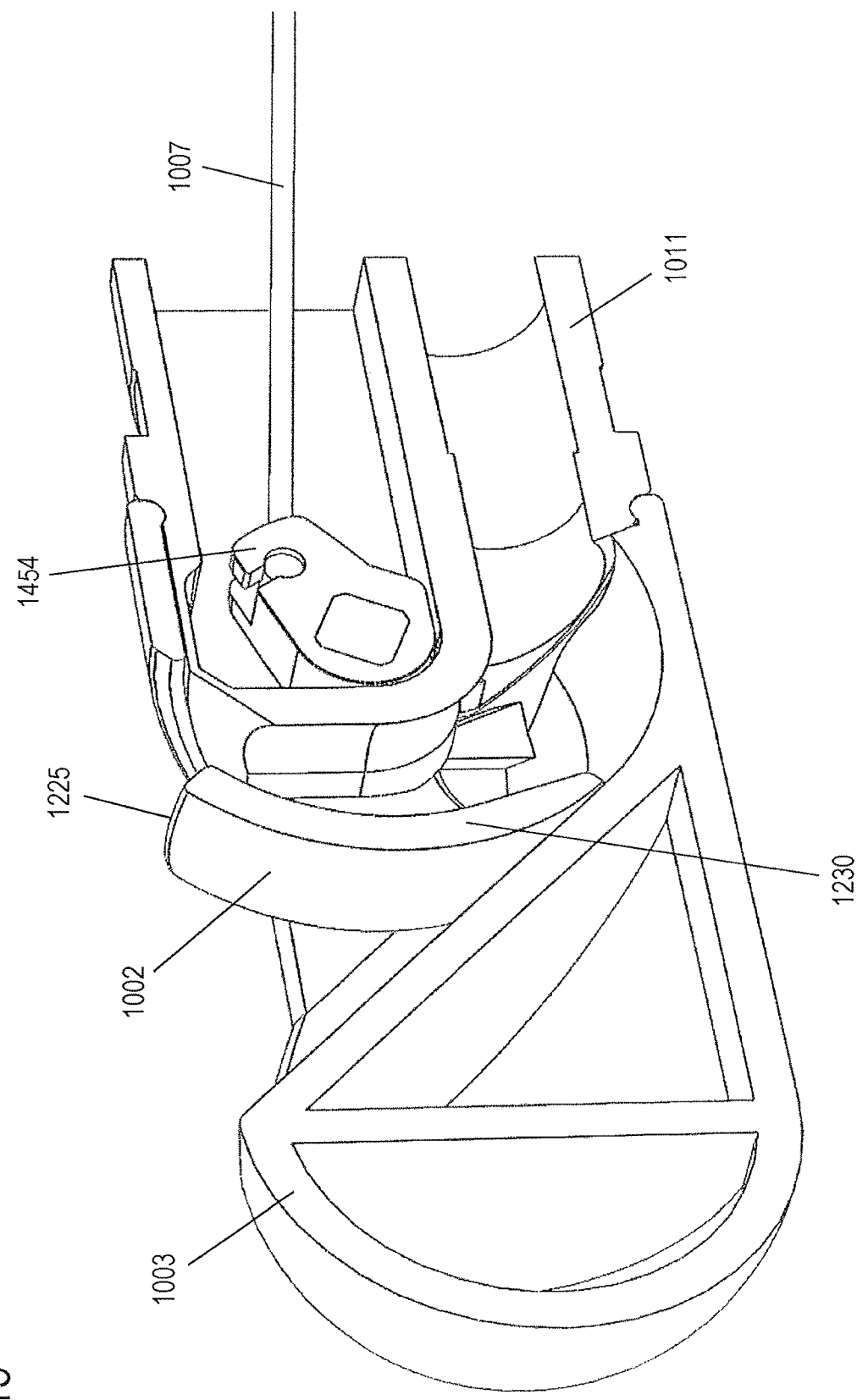
FIG. 15 shows a cut-open perspective view of the endoscope head of the second embodiment according to the present invention in a state in which the Albarran lever is completely swung out.

In its central portion, when viewed in the longitudinal direction, the endoscope head body 1011 comprises an opening facing sideways, i.e. extending perpendicular to the longitudinal axis of the endoscope head body 1011. Into this opening, a rotation shaft 1451 is inserted as a shaft body for the pivot lever 1045. Thus, the opening forms a bearing for the rotation shaft 1451. With respect to its opening, the rotation shaft 1451 is sealed, for example, by means of one or more ring seals. The rotation shaft 1451 extends into the inside of the endoscope head body 1011, in particular into the control wire channel 1015, see FIG. 13. At the inner end of the rotation shaft 1451, the rotation shaft 1451 is provided with an activation lever 1454 mounted on the axis of the rotation shaft 1451 in a form-fitting manner, as shown in FIGS. 13 to 15. At its end opposite to the rotation shaft 1451, the activation lever 1454 comprises a control wire barrel receiving member 1455 as a force receiving member by which a pulling force of a control wire 1007 can be applied to the activation lever 1454. A control wire barrel 1071 of the control wire 1007 is inserted into the control wire barrel receiving member 1455. The control wire barrel receiving member 1455 is formed in the shape of a hook retaining the control wire barrel 1071 rotatable relative to the activation lever 1454.

At its outer end, the rotation shaft 1451 is integrally formed in the flat shape of a cuboid forming the pivot lever 1045. In particular, the pivot lever 1045 and the rotation shaft 1451 are formed as a unit insertable into the endoscope head body 1011 from the outside. From the inside, the activation lever 1454 is slid onto the same.

At its flat cuboid shape, the pivot lever 1045 comprises two surfaces 1453 opposite to each other and extending horizontally in the rest position. At the distal and the proximal end surface of the flat cuboid shape, the pivot lever 1045 is rounded, as shown in FIG. 10, so that the surfaces 1453 on the distal and the proximal side merge into a respective radius.

In the endoscope head body 1011, the control wire channel 1015 forms a space which, on the distal side of the endoscope head body 1011, is sealed against the surrounding.

Cap 1003 with Albarran lever 1002 installed therein

The cap 1003 is formed as a cylinder provided with a bottom, with the bottom of the cap 1003 being located on the distal side and being rounded on the outside such that, when the cap 1003 has been placed on the endoscope head body 1011, it can be inserted into an object to be examined.

The cap 1003 comprises an opening 1031 facing upwards in FIG. 10. When using the endoscope head 1001, the opening 1031 of the cap 1003 forms an open lateral window for the tools guided through the working channel 1013.

At a distance to the proximal opening end, the cap 1003 comprises a lateral bore serving as a bearing for the Albarran lever 1002.

The Albarran lever 1002 is designed like a shovel and has a fulcrum. More particularly, the Albarran lever 1002 comprises an Albarran lever main body 1201 turning into a shovel 1230 on its lower side in FIGS. 12 and 13. Starting from the Albarran lever main body 1201, the shovel is bent to one side. On the proximal side, the shovel 1230 has a flat shovel portion 1231 and on the distal side, it has a bent shovel portion 1232. On the inner side, the flat shovel portion 1231 and the bent shovel portion 1232 form a guiding surface for guiding tools, etc., which are guided from the working channel 1013 towards the Albarran lever 1002.

Thus, this guiding surface forms an extension portion of the working channel 1013. The guiding surface formed of the flat shovel portion 1231 and the bent shovel portion 1232 is an inner surface of the shovel 1230 and is curved concavely. In a view from the side, the flat shovel portion 1231 extends tangentially from the bent shovel portion 1232 to the exit of the working channel 1013. When the Albarran lever 1002 is in the rest position in which it is not pivoted, the Albarran lever 1002 abuts on the endoscope head body 1011 such that the flat shovel portion 1231 and the distal exit area of the working channel 1013 on the bottom side in FIG. 13 (on the side of the endoscope head body 1011 which is radially opposite to the pivot lever 1045) are preferentially flush without a shoulder. As a consequence, tools from the working channel 1013 can be advanced unhindered to the flat shovel portion 1231.

On the side opposite to the shovel 1230, an insertion groove 1210 is provided in the Albarran lever main body 1201, as shown in FIG. 12. In the rest position of the Albarran lever 1002, the insertion groove 1210 extends horizontally i.e. in the longitudinal direction of the endoscope head 1001.

As shown in FIG. 12, the insertion groove 1210 is defined by two parallel contact surfaces 1222 facing each other, of which only the lower one is shown in FIG. 12. The upper contact surface is provided on the lower side of an upper portion 1202 of the Albarran lever 1002. The pivot lever 1045 is inserted into the insertion groove 1210 having the two parallel contact surfaces 1222. In the inserted state, the pivot lever 1045 is seated in the insertion groove 1210 such that the contact surfaces 1222 of the insertion groove 1210 face the surfaces 1453 of the pivot lever 1045.

On the opposite side of the shovel 1230, the Albarran lever main body 1201 is provided with a pivot projection 1026 in the area of the insertion groove 1210, the pivot projection 1026 extending from the Albarran lever main body 1201 in the direction opposite to the extension direction of the shovel 1230. The pivot projection 1026 is formed as a cylinder. The outer diameter of the pivot projection 1026 is selected such that the pivot projection 1026 is easily rotatable in the lateral bore of the cap 1003 serving as a bearing. For example, the outer diameter of the pivot projection 1026 can be slightly smaller than the inner diameter of the lateral bore of the cap 1003. The pivot projection 1026 of the Albarran lever 1002 is inserted into the lateral bore of the cap 1003, as is shown in FIG. 10.

Application of the Embodiment

Similar as in the first embodiment, the cap 1003 can be placed on the endoscope head body 1011.

The endoscope head body 1011 and the cap 1003 can be provided with a groove/nose similar to the groove 12 and the nose 32 of the first embodiment. Alternatively, a ring projection 1019 at an outer circumference of the endoscope head body 1011 can have such an outer diameter that it is in a firm force fit with the inner diameter of the cap 1003 when the cap 1003 has been slid onto the endoscope head body 1011. In a further alternative, the outer surface of the ring projection 1019 can be provided with grooves or indentations to establish an even stronger force fit with the inner surface of the cap 1003.

The cap 1003 is slid onto the endoscope head body 1011 with the pivot lever 1045 being simultaneously slid into the insertion groove 1210 of the Albarran lever 1002. In doing so, the pivot lever 1045 enters into the insertion groove 1210 in such a manner that its upwards and downwards directed insertion surfaces 1453 face the contact surfaces 1222 of the Albarran lever 1002. According to the present invention, in the position in which the cap 1003 is placed on the endoscope head body 1011 and is ready for use, the rotation shaft 1451 and the pivot projection 1026 are aligned axially.

FIGS. 13 to 15 show the pivoting operation of the Albarran lever of the second embodiment in a situation in which the Albarran lever is in the rest position, in a situation in which the Albarran lever is in an intermediate position, and in a situation in which the Albarran lever is in a position completely swung out.

FIG. 13 shows the rest position of the Albarran lever 1002. The activation lever 1454 extends from the rotation shaft 1451 substantially at a right angle radially to the outside (upwards in FIG. 13). In this position, the barrel 1071 of the control wire 1007 does not apply any load to the activation lever 1454. The shovel 1230 of the Albarran lever 1002 abuts on the endoscope head body 1011 at the distal exit of the working channel 1013.

When the control wire 1007 is pulled on the proximal side, the activation lever 1454 is pivoted about its fulcrum formed in the shaft body 1451, see the intermediate position in FIG. 14. The shaft body 1451 and, thus, the pivot lever 1045 rotate (pivot) in a corresponding manner. The rotation (pivoting) of the pivot lever 1045 seated in the insertion groove 1210 of the Albarran lever 1002 in turn causes the pivoting operation of the Albarran lever 1002. The proximal end of the Albarran lever 1002 moves away from the distal exit of the working channel 1013 at the endoscope head body 1011.

When the control wire 1007 is pulled further on the proximal side, the activation lever 1454 arrives at its completely swung-out end position, see FIG. 15. Although not shown in FIG. 15, the shovel 1230 of the Albarran lever 1002 can be so long that in the end position, the distal end 1025 of the shovel 1230 of the Albarran lever 1002 can be pivoted about the pivot axis 1451 of the pivot member 1045 to such an extent that it arrives at a position which, when seen in the longitudinal direction of the endoscope head body 1011, is proximally relative to the pivot axis 1451 of the pivot member 1045.

Advantages of the Embodiment

There are advantages similar to the first embodiment.

Since the side supporting member 4 of the first embodiment can be omitted and the pivot member 1045 is integrated in the endoscope head body 1011, the outer surface of the endoscope head body 1011 exhibits even less undercuts and can consequently be cleaned even more easily.

The cap 1003 and the Albarran lever 1002 form a common assembly which can be separated from the endoscope head body 1011 and can be designed as an assembly for single use.

Since in the pivot end position of the Albarran lever 1002, the distal end 1025 of the shovel 1230 can be positioned proximally relative to the pivot axis 1451 of the pivot member 1045, when seen in the longitudinal direction of the endoscope head body 1011, an exit angle of much more than 90° can be achieved for tools. In this way, the user has a much greater scope of operation. For instance, the introduction of a tool, for example into the bile duct, is significantly facilitated when the endoscope head body is positioned in the duodenum opposite the exit of the bile duct.

Further Alternatives

The endoscope head body 11 of the first embodiment comprises the locking groove as a groove 12 into which the circumferential locking nose 32 engages. In order to allow locking of the cap 3 at the endoscope head body 11, it is not necessary for the groove 12 to be provided as a circumferential groove, but it can also extend only at portions of the circumference of the endoscope head body 11. Instead of the groove 12, one or more locking indentations may be provided at the circumference of the endoscope head body 11. Then, instead of the circumferential locking nose 32, one or more locking projections protruding radially inwards can be provided on the proximal side of the cap, the locking projections being adapted to the locking indentations at the circumference of the endoscope head body 11 with respect to position and shape. In this way, when sliding the cap 3 onto the endoscope head body 11, an exact positional relation of the cap 3 relative to the endoscope head body 11 can be predefined.

At the endoscope head 1 of the first embodiment, the locking groove extends as a circumferential locking groove composed of a groove portion of the groove 12 at the endoscope head body 11 and a groove portion of the groove 415 of the side supporting member 4. The structure can be modified such that a locking groove is provided only at the circumference of the endoscope head body 11.

In the first embodiment, the side supporting member 4 is arranged at the endoscope head body 11 in such a manner that the proximal end faces 411 and 431 thereof are glued to the attachment surface 19. The invention is not limited to such a structure. The side supporting member 4 can also be formed such that on its proximal side, it comprises a locking means for locking with the attachment surface 19. For example, the attachment surface 19 can comprise distally extending pins which can be inserted into corresponding holes at the proximal end face(s) 411 and/or 431.

In the first embodiment, the insertion surfaces 453 of the arm 452 and the contact surfaces 222 of the fork portion 22 which, in the installed position of the Albarran lever at the pivot lever, are arranged opposite the insertion surfaces 453, are shown as flat surfaces. The insertion surfaces 453 and the opposing contact surfaces 222 can comprise grooves/indentations adapted to each other and extending in the longitudinal direction of the endoscope head to allow a more exact definition of the positional relation between the insertion surfaces 453 and the contact surfaces 222.

Other types of connections between the arm 452 and the fork portion 22; the pivot member 1045 and the Albarran lever main body 1201 are possible. For example, the Albarran lever can be attached to the pivot member by means of a click-on or latching connection, by means of sufficiently high static friction between the contact surfaces facing each other, by means of a hook device, etc.

In a further modification, the Albarran lever can be screwed to the pivot member or can be connected thereto by a splint or a pin, etc.

In the second embodiment, the guiding surface at the inner surface of the shovel 1230 is formed by the flat shovel portion 1231 and the bent shovel portion 1232. The flat shovel portion 1231 can be omitted. Preferentially, in a rest position of the Albarran lever 1002, the Albarran lever 1002 then abuts on the endoscope head body 1011 such that the bent shovel portion 1232 and the distal exit portion of the working channel 1013 are preferably flush without a shoulder, as can be seen on the bottom of FIG. 13. Thus, also in the second embodiment, the shovel inner surface 1232 can be curved such that it forms a tangent from the straight working channel end portion of the endoscope head body 1011 to the curved shovel inner surface 1232 forming the working channel extension portion of the Albarran lever 1002.

Alternatively, in the second embodiment, the Albarran lever 2 of the first embodiment can be used.

The Albarran lever 2; 1002 and the cap 3; 1003 do not need to form a common assembly. As an alternative, the structure can be selected such that the Albarran lever is relatively displaceable at the pivot member, independently from the cap. In the cap, the lever holder 34 of the first embodiment and the lateral bore of the second embodiment can then be omitted. In this alternative, first the Albarran lever is attached to the pivot member, and then the cap is placed on the endoscope head body.

In a further modification, a fork portion, such as the fork portion 22, can be provided on the pivot member, and an arm, such as the arm 452, can be provided on the Albarran lever.

The invention cannot only be applied in a duodenoscope. The principle of the invention can also be applied in an ultrasound endoscope.

In the embodiments, one working channel is shown with an Albarran lever at the end of the working channel. The invention is also applicable in endoscopes comprising a plurality of working channels, each having one Albarran lever at the end of the respective working channel.

The alternatives discussed above can be combined and can be applied in all embodiments.

LIST OF REFERENCE SIGNS 1 endoscope head
2 Albarran lever
3 cap
4 side supporting member (supporting member)
5 ring seal (sealing member)
11 endoscope head body
12 locking groove
13 working channel
15 control wire channel
16 camera
17 illumination means
18 attachment surface for the side supporting member 4
19 attachment surface
21 Albarran lever main body
22 fork portion of the Albarran lever
24 working channel inner surface of the Albarran lever
25 distal end of the working channel inner surface
26 pivot projection
27 slit
31 working channel end opening of the cap
32 locking nose of the cap
34 lever holder
35 bore
41 outer member
42 gap
43 inner member
44 receiving bore
45 pivot lever (pivot member)
131 inner surface for the working channel member
133 curved portion of the working channel
137 radial contact surface
221 insertion surface
222 contact surface
411 proximal (end) face
415 groove
431 proximal (end) face
432 curve-shaped member
433 reinforcement portion
451 rotation shaft of the pivot lever (axis of the pivot member)
452 arm
453 insertion surface
454 activation lever
455 control wire barrel receiving member (force receiving member)
1001 endoscope head
1002 Albarran lever
1003 cap
1007 control wire
1011 endoscope head body
1013 working channel
1015 control wire channel
1016 camera
1017 illumination means
1019 ring projection
1026 pivot projection
1031 opening
1045 pivot lever
1071 control wire barrel
1201 Albarran lever main body
1202 upper portion
1210 insertion groove
1222 contact surface
1225 distal end
1230 shovel
1231 flat shovel portion
1232 curved shovel portion
1451 rotation shaft of the pivot lever (axis of the pivot member)
1453 surface
1454 activation lever
1455 control wire barrel receiving member (force receiving member)

What is claimed is:

1. An endoscope comprising an endoscope head body in which at least one working channel is formed, wherein,
said endoscope head body comprises:
an extension portion which extends from the endoscope head body towards a distal side, wherein at the extension portion a camera or an illumination means is provided;
a supporting member which extends from the endoscope head body towards a distal side, wherein the supporting member is separate and detachable from the endoscope head body, wherein at the supporting member a receiving bore is provided on a surface of the supporting member;
a pivot member inserted into said receiving bore, wherein at the pivot member a pivot lever arm and a rotation shaft are provided, and wherein said rotation shaft is rotatably supported at said supporting member, and said rotation shaft is actuatable from a proximal side; and
an Albarran lever detachably mountable to and demountable from said pivot lever arm,
wherein said pivot lever arm projects from said supporting member towards said extension portion, wherein the endoscope head further comprises a cap which can be distally slid onto the endoscope head, wherein said Albarran lever is arranged inside said cap such that the Albarran lever pivots relative to said cap, and said cap comprises an opening which corresponds to said endoscope head body, and wherein when said cap is sliding from the endoscope head to the distal direction, said Albarran lever is displaced from the pivot lever arm.

2. The endoscope according to claim 1, wherein said rotation shaft is cylindrical.

3. The endoscope according to claim 1, wherein said endoscope head body comprises a control wire channel, and said Albarran lever is actuatable from a proximal side by a control wire guided into said control wire channel.

4. The endoscope according to claim 3, wherein said pivot member comprises an activation lever which extends from another end of said rotation shaft towards a direction crossing an axis of said rotation shaft, said another end of said rotation shaft being opposite to the end of said rotation shaft from which said pivot lever arm extends, and said activation lever comprises a force receiving member into which said control wire is fittable.

5. The endoscope according to claim 1, wherein said pivot lever arm does not contact said extension portion.

6. The endoscope according to claim 1, wherein a sealing member is arranged between said rotation shaft and said receiving bore.

7. The endoscope according to claim 1, wherein said Albarran lever is formed as a shovel whose distal end can be pivoted about said rotation shaft up to a location which, when viewed in a longitudinal direction of said endoscope head body, is provided proximally relative to said rotation shaft.

8. The endoscope according to claim 1, wherein said Albarran lever is formed as a shovel whose inner surface forms an extension portion of the working channel, wherein said shovel inner surface is curved such that it forms a tangent from a straight working channel end portion of said endoscope head body towards the curved shovel inner surface which forms the working channel extension portion of said Albarran lever.

9. The endoscope according to claim 1, wherein said Albarran lever is detachably mountable to and demountable from said pivot lever arm without the use of tools.

10. The endoscope according to claim 1, wherein said Albarran lever is detachably mountable to and demountable from said pivot lever arm with the use of tools.

11. The endoscope according to claim 1, wherein said endoscope head body comprises a groove on its outer circumferential surface, and said cap projects inwardly and comprises a locking nose which can be locked in said groove.

12. The endoscope according to claim 1, wherein said pivot lever arm, together with said supporting member, forms a common assembly detachable from and mountable to said endoscope head body, wherein in an operational state, said common assembly is surrounded by said cap.

13. The endoscope according to claim 1, wherein the endoscope head further comprises a cap which can be distally slid onto the endoscope head, wherein in said cap the Albarran lever is arranged such that it can be pivoted relative to the cap, and said cap comprises an opening which corresponds to said endoscope head body, and the Albarran lever and the cap form a common assembly which, on the distal side of the endoscope head body, is detachably mountable as a unit.

14. The endoscope according to claim 1, wherein said Albarran lever is arranged between said supporting member and said extension portion.

15. The endoscope according to claim 1, wherein said Albarran lever is displaceable in a distally slidable manner relative to said pivot lever arm.

16. An endoscope comprising an endoscope head body in which at least one working channel is formed, wherein, said endoscope head body comprises:

an extension portion which extends from the endoscope head body towards a distal side, wherein at the extension portion a camera or an illumination means is provided;

a supporting member which extends from the endoscope head body towards a distal side, wherein the supporting member is separate and detachable from the endoscope head body, wherein at the supporting member a receiving bore is provided on a surface of the supporting member;

a pivot member inserted into said receiving bore, wherein at the pivot member a pivot lever arm and a rotation shaft are provided, and wherein said rotation shaft is rotatably supported at said supporting member, and said rotation shaft is actuatable from a proximal side; and an Albarran lever detachably mountable to and demountable from said pivot lever arm, wherein said pivot lever arm projects from said supporting member towards said extension portion, wherein the endoscope head further comprises a cap which can be distally slid onto the endoscope head, wherein in said cap the Albarran lever is arranged such that it can be pivoted relative to the cap, and said cap comprises an opening which corresponds to said endoscope head body, and wherein the Albarran lever and the cap form a common assembly which, on the distal side of the endoscope head body, is detachably mountable as a unit.

17. The endoscope according to claim 16, wherein the endoscope head further comprises a cap which can be distally slid onto the endoscope head, wherein said Albarran lever is arranged inside said cap such that the Albarran lever pivots relative to said cap, and said cap comprises an opening which corresponds to said endoscope head body, and when said cap is sliding from the endoscope head to the distal direction, said Albarran lever is displaced from the pivot lever arm.

18. The endoscope according to claim 17, wherein said endoscope head body comprises a groove on its outer circumferential surface, and said cap projects inwardly and comprises a locking nose which can be locked in said groove.

19. The endoscope according to claim 17, wherein said pivot lever arm, together with said supporting member, forms a common assembly detachable from and mountable to said endoscope head body, wherein in an operational state, said common assembly is surrounded by said cap.

20. The endoscope according to claim 16, wherein
said endoscope head body comprises a control wire channel, and
said Albarran lever is actuatable from a proximal side by a control wire guided into said control wire channel.

\* \* \* \* \*